US009914753B2

(12) United States Patent
Krishna et al.

(10) Patent No.: US 9,914,753 B2
(45) **Date of Patent: *Mar. 13, 2018**

(54) PEPTIDE COMPOUNDS TO REGULATE THE COMPLEMENT SYSTEM

(71) Applicants: Eastern Virginia Medical School, Norfolk, VA (US); Children's Health Foundation, Inc., Norfolk, VA (US); Eriko Life Sciences Ventures, LLC, Norfolk, VA (US)

(72) Inventors: Neel K. Krishna, Norfolk, VA (US); Kenji Cunnion, Norfolk, VA (US)

(73) Assignees: Eastern Virginia Medical School, Norfolk, VA (US); Children's Health Foundation, Inc., Norfolk, VA (US); Eriko Life Sciences Ventures, LLC, Norfolk, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/203,469

(22) Filed: Jul. 6, 2016

(65) Prior Publication Data

US 2016/0311856 A1 Oct. 27, 2016

Related U.S. Application Data

(60) Continuation of application No. 14/536,073, filed on Nov. 7, 2014, now Pat. No. 9,422,337, which is a division of application No. 13/809,371, filed as application No. PCT/US2011/044791 on Jul. 21, 2011, now Pat. No. 8,906,845.

(60) Provisional application No. 61/366,204, filed on Jul. 21, 2010.

(51) Int. Cl.

| | |
|---|---|
| ***C07K 7/08*** | (2006.01) |
| ***C07K 14/005*** | (2006.01) |
| ***A61K 38/16*** | (2006.01) |
| ***A61K 45/06*** | (2006.01) |
| ***C07K 14/08*** | (2006.01) |
| *A61K 38/03* | (2006.01) |
| *A61K 38/17* | (2006.01) |
| *A61K 38/00* | (2006.01) |

(52) U.S. Cl.

CPC .............. *C07K 7/08* (2013.01); *A61K 38/162* (2013.01); *A61K 45/06* (2013.01); *C07K 14/005* (2013.01); *C07K 14/08* (2013.01); *A61K 38/00* (2013.01); *A61K 38/03* (2013.01); *A61K 38/1725* (2013.01); *C12N 2770/12022* (2013.01); *C12N 2770/12033* (2013.01)

(58) Field of Classification Search

CPC .. A61K 38/03; A61K 38/162; A61K 38/1725; A61K 45/06; C07K 14/005; C07K 14/08; C07K 7/08; C12N 2770/12022; C12N 2770/12033

See application file for complete search history.

(56) References Cited

U.S. PATENT DOCUMENTS

| | | | |
|---|---|---|---|
| 6,126,939 | A | 10/2000 | Eisenbach-Schwartz et al. |
| 6,696,562 | B1 | 2/2004 | Schultz-Cherry et al. |
| 7,381,524 | B2 | 6/2008 | Schultz-Cherry et al. |
| 8,241,843 | B2 | 8/2012 | Krishna et al. |
| 2005/0079485 | A1 | 4/2005 | Schultz-Cherry et al. |
| 2007/0012617 | A1 | 1/2007 | Suzuki et al. |
| 2009/0092581 | A1 | 4/2009 | Skawinski et al. |
| 2010/0055106 | A1 | 3/2010 | Krishna et al. |
| 2011/0104156 | A1 | 5/2011 | Christadoss et al. |
| 2013/0244924 | A1 | 9/2013 | Krishna et al. |
| 2014/0309175 | A1 | 10/2014 | Zhao et al. |
| 2015/0031599 | A1 | 1/2015 | Abuchowski et al. |
| 2015/0064176 | A1 | 3/2015 | Schwaeble et al. |

FOREIGN PATENT DOCUMENTS

| | | |
|---|---|---|
| WO | WO-9426902 | 11/1994 |
| WO | WO-9944625 | 9/1999 |
| WO | WO-0043027 | 7/2000 |
| WO | WO-2005023195 | 3/2005 |
| WO | WO-2005023296 | 3/2005 |

(Continued)

OTHER PUBLICATIONS

Human Astrovirus 1, Accession No. S68561.1, GENBANK, accessed on Jul. 22, 2016.*

Noris and Remuzzi, "Overview of Complement Activation and Regulation," Semin. Nephrol. 33(6), pp. 479-492 (2013).

Bass et al., "Proteolytic processing of the astrovirus capsid," J. of Virol. 74(4), pp. 1810-1813 (2000).

Bass et al., "Characterization of Human Serotype 1 Astrovirus-Neutralizing Epitopes," Journal of Virology, Nov. 1997, pp. 8666-8671.

Bonaparte et al., "Human astrovirus coat protein inhibits serum complement activation via C1, the first component of the classical pathway," J. of Virol. 82(2), pp. 817-827 (2008).

Caballero et al., "Structural requirements of astrovirus virus-like particles assembed in insect cells," J. of Virol. 78(23), pp. 13285-13292 (2004).

(Continued)

*Primary Examiner* — Hasan S Ahmed
*Assistant Examiner* — Erinne R Dabowski
(74) *Attorney, Agent, or Firm* — Wilmer Cutler Pickering Hale and Dorr LLP

(57) ABSTRACT

The present invention provides peptide compounds that regulate the complement system and methods of using these compounds. The invention is an isolated, purified peptide of 30 amino acids derived from human astrovirus protein, called CP1. The invention is directed to peptide compounds that are peptide mimetics, peptide analogs and/or synthetic derivatives of CP1 having, for example, internal peptide deletions and substitutions, deletions and substitutions at the N-terminus and C-terminus, and that are able to regulate complement activation. The invention further provides pharmaceutical compositions of therapeutically effective amounts of the peptide compounds and a pharmaceutically acceptable carrier, diluent, or excipient for treating a disease or condition associated with complement-mediated tissue damage.

4 Claims, 9 Drawing Sheets

(56) References Cited

FOREIGN PATENT DOCUMENTS

| | | | |
|---|---|---|---|
| WO | WO 2007145806 A2 * | 12/2007 | .......... C07K 14/005 |
| WO | WO-2012012600 | 1/2012 | |

OTHER PUBLICATIONS

Carvalho and Gomes, "Plant defensins—prospects for the biological functions and biotechnological properties," Peptides, vol. 30, pp. 1007-1020 (2009).

Castellano et al., "Therapeutic targeting of classical and lectin pathways of complement protects from ischemia-reperfusion-induced renal damage," Amer. J. Pathol., vol. 176, pp. 1-12 (2010).

Cooper, "The classical complement pathway: activation and regulation of the first complement component," Adv. Immunol. 73, pp. 151-216 (1985).

Cunnion et al., "Capsule production and growth phase influence binding of complement to *Staphylococcus aureus*," Infect. Immun., vol. 69, pp. 6796-6803 (2001).

Dong et al., "Particle polymorphism caused by deletion of a peptide molecular switch in a quasiequivalent icosahedra virus," J. Virol. 72:7, pp. 6024-6033 (1998).

Favoreel et al., "Virus complement evasion strategies," Journal of General Virology, 84, pp. 1-15 (2003).

Fogh, et al., "Human tumor cells in vitro," Plenum Press, pp. 115-159 (1975).

Fryer, et al., "Synthetic peptides which inhibit the interaction between C1q and immunoglobulin and prolong xenograft survival," Transplantation, vol. 70, pp. 828-836 (2000).

Geigemuller et al., "Construction of a genome-lenght cDNA clone for human astrovirus serotype 1 and synthesis of infectious RNA transcripts," J. Virol. 71, pp. 1713-1717 (1997).

GenBank, "Human Astrovirus Putative Serine Protease Gene, Complete cds; Putative RNA-Dependent RNA Polymerase Gene, Partial cds; and Capsid Precursor Protein Gene, Complete cds," Jun. 2001, retrieved from http://www.ncbi.nlm.nih.gov/nuccore/AF141381 on Nov. 24, 2011, (3 pages).

GenBank, "Human Astrovirus Type 1 Genes for Capsid Protein and Nonstructural Protein," retrieved on May 15, 2013 from http://www.ncbi.nlm.nih.gov/nuccore/z25771, 5 pages.

Groeneveld et al., "Human neutrophil peptide-1 inhibits both the classical and the lectin pathway of complement activation," Molec. Immunol. vol. 44, pp. 3608-3614 (2007).

Hair et al., "Human astrovirus coat protein binds C1q and MBL and inhibits the classical and lectin pathways of complement activation," Molecular Immunology 47, pp. 792-798 (2010).

Huwiler et al., "Optimizing the MALDI-TOF-MS observation of peptides containing disulphide bonds," J. Biomolec. Tech. vol. 14, pp. 289-297 (2003).

International Search Report and Written Opinion for International Application No. PCT/US2007/012617, dated May 12, 2008 (11 pages).

International Search Report and Written Opinion for International Application No. PCT/US2011/044791, dated Feb. 2, 2012 (14 pages).

Kohno et al., "Development of Simple Latex Agglutination Test for Detection of Astrovirus Serotype 1," JARMAM vol. 11(2), pp. 87-91 (2000).

Kojima et al., "Inhibition of complement-mediated immune hemolysis by peptides derived from the constant domain of immunoglobulin," Transplantation vol. 67, pp. 637-638 (1999).

Krishna et al., "Human Astrovirus Coat Protein: A Novel C1 Inhibitor," Current Topics in Complement II; Advances in Experimental Medicine and Biology, Springer Science+Business Media, LLC, pp. 237-251 (2008).

Krishna, "Identification of structural domains involved in astrovirus capsid biology," Virol. Immunol. 18:1, pp. 17-26 (2005).

Larkin, "Clustal W and Clustal X version 2.0," Bioinformatics, vol. 23, pp. 2947-2948 (2007).

Lauvrak et al., "Identification and characterization of C1q-binding phage displayed peptides," Biol. Chem. vol. 378, pp. 1509-1519 (1997).

Lee et al., "Early complement factors in the local tissue immunocomplex generated during intestinal ischemia/reperfusion injury," Mol. Immunol. vol. 47, pp. 972-981 (2010).

Liu et al., "Solution structure of the plant defensin VrD1 from mung bean and its possible role in insecticidal activity against bruchids," Proteins vol. 63, pp. 777-786 (2006).

Lund et al., "CPHmodels 2.0: X3M a Computer Program to Extract 3D Models," Abstract at the CASP5 conference A102 (2002).

Mallik et al, "Design and NMR characterization of active analogs of Compstatin containing non-natural amino acids," J. Med. Chem. vol. 48, pp. 274-286 (2005).

Mendez-Toss et al., "Molecular Analysis of a Serotype 8 Human Astrovirus Genome," Journal of General Virology 81, pp. 2891-2897 (2000).

Messmer et al., "Sequential determination of ligands binding to discrete components in heterogeneous mixtures by iterative panning and blocking (IPAB)," J. Mol. Biol. vol. 296, pp. 821-832 (2000).

Morgan et al., "Complement therapeutics; history and current progress," Molec. Immunol. 40, pp. 159-170 (2003).

Ricklin and Lambris, "Complement-targeted therapeutics," Nat. Biotech. vol. 25, pp. 1265-1275 (2007).

Roos et al., "Specific inhibition of the classical complement pathway by C1q-binding peptides," J. Immunol., vol. 167, pp. 7052-7059 (2001).

Sahu et al., "Inhibition of complement by a C3-binding peptide isolated from a phage-displayed random peptide library," J. Immunol. vol. 157, pp. 884-891 (1996).

Sambrook et al., "Molecular cloning: a laboratory manual, 3rd ed." Cold Spring Harbor Laboratory Press, 21 pages (2001).

Scheneemann et al. "Use of recombinant baculoviruses in synthesis of morphologically distinct viruslike particles of flock house virus, a nodavirus," J. Virol. 67, pp. 2756-2763 (1993).

ScienceDaily, "Research could lead to way to halt deadly immune response." (Available online at http://www.sciencedaily.com/release/2010/021100209183127.htm) (Feb. 10, 2010) (2 pages).

Supplementary European Search Report issued by the European Patent Office for European Patent Application No. 07809212, search completed Aug. 27, 2010 (3 pgs.).

Taylor et al., "Structure—activity relationships in beta-defensin peptides," Biopolymers vol. 90, pp. 1-7 (2007).

Thermo Electron Corporation, N-Terminal Acetylation and C-Terminal Amidation of Peptides, Technical Information, Thermo Electron Corporation, 2004, online, retrieved on Feb. 2, 2012 from <http://www.greiner-bio-one.co.jp/products/peptides/acetylation__amidation.pdf> Description and Advantages, 2 pages.

Tjernberg et al., "Acute antibody-mediated complement activation mediates lysis of pancreatic islets cells and may cause tissue loss in clinical islet transplantation," Transplantation vol. 85, pp. 1193-1199 (2008).

Zhang et al., "NMR studies of defensin antimicrobial peptides. 1. Resonance assignment and secondary structure determination of rabbit NP-2 and human HNP-1," Biochemistry. vol. 31, pp. 11348-11356 (1992).

UniProtKB/TrEMBL, "Capsid Protein—Human Astrovirus-1 (HAstV-1)," Jul. 22, 2008, retrieved from <http://www.uniprot.org/uniprot/A9CE26> on Nov. 23, 2011, 3 pages.

van den Berg et al., "Inhibition of activation of the classical pathway of complement by human neutrophil defensins," Blood vol. 92, pp. 3898-3903 (1998).

Vaughn et al., "The establishment of two cell lines from the insect Spodoptera frugiperda (Lepidoptera; Noctuidae," In Vitro 13, pp. 213-217 (1977).

Willcocks et al., "Growth and characterisation of human faecal astrovirus in a continuous cell line," Arch. Virol. 113, pp. 73-81 (1990).

Younger et al., "Systemic and lung physiological changes in rats after intravascular activation of complement," J. Appl. Physiol. 90, pp. 2289-2295 (2001).

(56) References Cited

OTHER PUBLICATIONS

Zhang et al., “Activation of the lectin pathway by natural IgM in a model of ischemia/reperfusion injury,” J. Immunol. vol. 177, pp. 4727-4734 (2006).
Gronemus et al., “Potent inhibition of the classical pathway of complement by a novel C1g-binding peptide derived from the human astrovirus coat protein,” Molecular Immunology, vol. 48, pp. 305-313 (2010).
Park et al., “A Readily Applicable Strategy to Convert Peptides to Peptoid-based Therapeutics,” vol. 8, issue. 3, e58874, pp. 1-7 (2013).
Harris and Chess, “Effect of pegylation on pharmaceuticals,” Nature Reviews Drug Discovery, vol. 2, 214-221 (Mar. 2003).
Sharp et al., “Peptide inhibitor of complement C1, a novel suppressor of classical pathway activation: mechanistic studies and clinical potential,” Frontiers in Immunology, vol. 5, article 406, 9 pages (Aug. 22, 2014).

* cited by examiner

```
CP      79 PAICQRATATLGTVGSNTSGTTEIEACILLNPVLVKDATGSTQFGPVQALGAQYSMWKLKY  139 (SEQ ID NO: 36)
HNP-1    0 ACYCR-------------------IPACI----------AGERRYGTCIYQG---RLWAFCC     30 (SEQ ID NO: 37)
           ., *:                   * ***          :*. ::*.     *    :* :
CP1        PAICQRATATLGTVGSNTSGTTEIEACILL (SEQ ID NO: 1)
CP2                                      NPVLVKDATGSTQFGPVQALGAQYSMWKLK (SEQ ID NO: 2)
```

```
E23A residues  2-29 AICQRATATLGTVGSNTSGTTAIEACIL  (SEQ ID NO: 5)
VrD1 residues 17-44 TTCAHSCKNRGYIGGNCKGMTRTCYCLV  (SEQ ID NO: 38)
                    : * ::  . * :*.* .* *    *::
```

PEPTIDE COMPOUNDS TO REGULATE THE COMPLEMENT SYSTEM

CROSS-REFERENCE TO RELATED APPLICATIONS

This application is a continuation of U.S. application Ser. No. 14/536,073, entitled "Peptide Compounds to Regulate the Complement System," filed Nov. 7, 2014, which is a division of U.S. application Ser. No. 13/809,371, entitled "Peptide Compounds to Regulate the Complement System," filed May 23, 2013 now U.S. Pat. No. 8,906,845 issued Dec. 9, 2014, which is a §371 of PCT/US2011/044791 entitled "Peptide Compounds to Regulate the Complement System," filed Jul. 21, 2011, which claims priority to U.S. Provisional Application No. 61/366,204 entitled "Peptide Compounds to Regulate the Complement System," filed Jul. 21, 2010, all of which are incorporated by reference herein.

STATEMENT REGARDING FEDERALLY SPONSORED RESEARCH

This invention was made with government support under Grant R21 AI060874 awarded by National Institutes of Health (NIH). The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 25, 2013, is named 0113019.270US1_SL.txt and is 13,348 bytes in size.

FIELD

The invention relates generally to the field of therapeutic intervention in inflammatory and autoimmune disease. More specifically, the invention relates to peptide compounds that can regulate complement activation and can be used therapeutically in the prevention and treatment of complement-mediated diseases, such as inflammatory, autoimmune and pathogenic diseases.

BACKGROUND

The complement system, an essential component of the innate immune system, plays a critical role as a defense mechanism against invading pathogens, primes adaptive immune responses, and helps remove immune complexes and apoptotic cells. Three different pathways comprise the complement system: the classical pathway, the lectin pathway and alternative pathway. C1q and mannose-binding lectin (MBL) are the structurally related recognition molecules of the classical and lectin pathways, respectively. Whereas IgM or clustered IgG serve as the principal ligands for C1q, MBL recognizes polysaccharides such as mannan. Ligand binding by C1q and MBL results in the sequential activation of C4 and C2 to form the classical and lectin pathway C3-convertase. In contrast, alternative pathway activation does not require a recognition molecule, but can amplify C3 activation initiated by the classical or lectin pathways. Activation of any of these three pathways results in the formation of inflammatory mediators (C3 and C5a) and the membrane attack complex (MAC), which causes cellular lysis.

While the complement system plays a critical role in many protective immune functions, complement activation is a significant mediator of tissue damage in a wide range of autoimmune and inflammatory disease processes. (Ricklin and Lambris, 2007).

A need exists for complement regulators. While the complement system is a vital host defense against pathogenic organisms, its unchecked activation can cause devastating host cell damage. Currently, despite the known morbidity and mortality associated with complement dysregulation in many disease processes, including autoimmune diseases such as systemic lupus erythematosus, myasthenia gravis, and multiple sclerosis, only two anti-complement therapies have recently been approved for use in humans: purified, human C1-Inhibitor licensed for use in patients suffering from hereditary angioedema (HAE) and Eculizumab/Solaris, a humanized, long-acting monoclonal antibody against C5 used in the treatment of paroxysmal nocturnal hemoglobinuria (PNH) Both PNH and HAE are orphan diseases in which very few people are afflicted; currently no complement regulators are approved for the more common disease processes in which dysregulated complement activation plays a pivotal role.

The Astroviridae constitute a family of non-enveloped, icosahedral viruses with a single-stranded, messenger-sense RNA genome. These viruses are a significant cause of gastroenteritis in humans as well as other diseases in other animal species. It is estimated that they cause an estimated 2-17% of children's diarrheal illness worldwide.

The astrovirus coat protein ("CP") has strong effects on the complement system, suggesting that the 'active' portion of the protein may have clinical utility in decreasing tissue damage from complement-mediated diseases. The wild type coat protein ("WP CP") purified from human astrovirus type 1 (HAstV-1) can bind C1q and MBL, and regulates both classical and lectin pathway activations (Hair et al., 2010. *Molec. Immunol.* 47, 792-798). This property is analogous to the properties described for human neutrophil peptide-1 (HNP-1) (van den Berg et al., 1998. *Blood.* 92, 3898-3903; Groeneveld et al., 2007. *Molec. Immunol.* 44, 3608-3614). The HAstV-1 coat protein is a 787 amino acid molecule that has been expressed from a recombinant baculovirus construct and then purified (Bonaparte et al., *J. Virol.* 82, 817-827).

Developing peptide compounds to inhibit classical, lectin and alternative pathways of the complement system are of interest, as each of these three pathways have been demonstrated to contribute to numerous autoimmune and inflammatory disease processes. Specific blockade of classical and lectin pathways are of particular interest, as both of these pathways have been implicated in ischemia-reperfusion induced injury in many animal models. (Castellano et al., 2010; Lee et al., 2010; Tjernberg, et al., 2008; Zhang et al. 2006). Humans with alternative pathway deficiencies suffer sever bacterial infections; thus, a functional alternative pathway is essential for immune surveillance against invading pathogens.

It would be desirable to develop peptide compounds that can regulate complement activation and can be used therapeutically to prevent and treat complement-mediated diseases, such as inflammatory, autoimmune and pathogenic diseases.

SUMMARY

The present invention provides peptide compounds that regulate the classical and lectin pathways of the complement system and methods of using these compounds. Specifically, the peptide compounds of this invention can bind, regulate and inactivate C1 and MBL, and therefore can efficiently inhibit classical and lectin pathway activation at its earliest point while leaving the alternative pathway intact. These peptide compounds are of therapeutic value for selectively regulating and inhibiting C1 and MBL activation without affecting the alternative pathway and can be used for treating diseases mediated by dysregulated activation of the classical and lectin pathways. In other embodiments, the peptide compounds regulate the classical pathway activation but not the lectin pathway activation.

The invention is based on the identification of an isolated, purified peptide of 30 amino acids derived from human astrovirus coat protein, termed CP1, and having SEQ ID NO:1 that is able to regulate the classical and lectin pathway activation by binding to C1q and MBL.

In other embodiments, the invention is directed to peptide compounds that are peptide mimetics, peptide analogs and/or synthetic derivatives of CP1 having, for example, internal peptide deletions and substitutions, deletions and substitutions at the N-terminus and C-terminus, and that are able to regulate the classical and lectin pathway activation by binding to C1q and MBL.

A further embodiment of the invention is any one of the peptide compounds of this invention, wherein the peptide compound is modified through acetylation of the N-terminal residue.

In some embodiments, the peptide sequence has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:1.

Another embodiment of the invention further provides pharmaceutical compositions. For example, the invention provides a pharmaceutical composition comprising a therapeutically effective amount of the peptide of any one of the compounds described above and at least one pharmaceutically acceptable carrier, diluent, or excipient.

Another embodiment of the invention further provides a method of regulating the complement system in a subject, comprising administering to the subject the composition described above.

A further embodiment of the invention is a method of treating a disease associated with complement-mediated tissue damage by administering the pharmaceutical compositions described above, wherein the disease associated with complement-mediated tissue damage is selected from the group consisting of rheumatoid arthritis, systemic lupus erythematosus, multiple sclerosis, myasthenia gravis, autoimmune hemolytic anemia, membranoproliferative glomerulonephritis, serum sickness, Adult Respiratory Distress Syndrome (ASDS), ischemia-reperfusion injury, stroke, myocardial infarction, allo- or xeno-transplantation injury, hyeracute rejection, graft versus host disease (GVHD), Alzheimer's disease, burn injuries, hemodialysis damage, cardiopulmonary bypass damage, paroxysmal pocturnal hemoglobinuria (PNH), and hereditary angioedema (HAE).

Another embodiment of the invention is a method of treating a disease associated with complement-mediated tissue damage, further comprising administering to a subject at least one other active ingredient effective in treating the disease, wherein the at least one other active ingredient is selected from the group consisting of a non-steroidal anti-inflammatory agent, a corticosteroid, a disease modifying anti-rheumatic drug, a C1-inhibitor, and eculizumab.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and claims.

BRIEF DESCRIPTION OF THE FIGURES

FIG. 2A also shows the two 30 amino acid peptides (CP1 and CP2) that were synthesized based upon this alignment.

In FIGS. 4A and 4B, the heavy and light chains of C1s, which indicate C1s activation, and the proenzyme C1s, are indicated to the right of the gel image, while the molecular mass markers (in kD) are indicated to the left of the gel image. FIGS. 4C and 4D are graphs quantifying the extent of C1 activation corresponding to CP1 (FIG. 4C) and CP2 (FIG. 4D), respectively, as determined by Odyssey imaging. Data are the means from two independent experiments. Error bars denote SEM.

In FIG. 6A, antibody-sensitized sheep erythrocytes were incubated with NHS alone, or with peptide compounds (1.4 mM) or a DMSO control. In FIG. 6B, antibody-sensitized sheep erythrocytes were incubated with NHS (white bars) or factor B-depleted serum (black bars) alone, or with peptide compounds (0.77 mM) or a DMSO control. Hemolysis was standardized to 100% for serum alone. FIG. 6A depicts the mean data from three independent experiments, and FIG. 6B depicts data from one experiment. Error bars denote SEM.

FIG. 8A depicts linear mode analysis of E23A, In FIG. 8A, the lower resolution and lower mass accuracy of the linear mode is shown in the zoom of the peptide peak with the lack of monoisotopic peptide peaks. In FIG. 8B, the high resolution and mass accuracy of the reflection mode is shown in the zoom of the peptide peak. In both FIGS. 8A and 8B, there are no major peaks with a mass to charge ratio (m/z) greater than the theoretical mass of the peptide.

DETAILED DESCRIPTION

Figure 1:
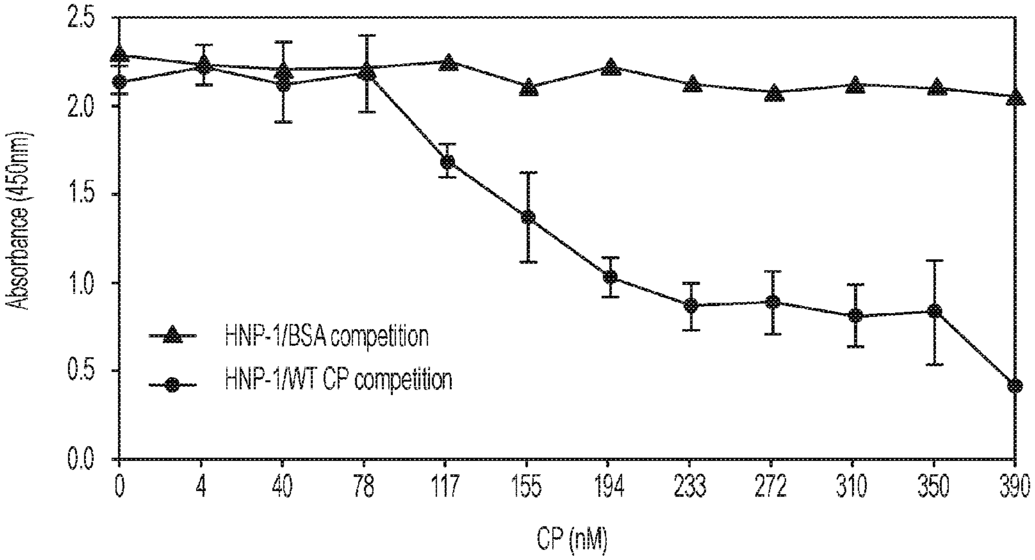
FIG. 1 is a graph depicting CP dose-dependently competing with human neutrophil defensin 1 (HNP-1) for binding to C1q. C1q was mixed with increasing amounts of WT CP (circles) or BSA (triangles) and added to the ELISA plate coated with HNP-1. After washing, bound C1q was measured using polyclonal antibody to C1q. Data are the means from three independent experiments. Error bars denote SEM.

The present invention provides peptide compounds that regulate the classical and lectin pathways of the complement system, specifically by binding and/or inactivating C1 and MBL and thus regulating the classical and lectin pathway activation at its earliest point without affecting the alternative pathway. These peptide compounds are of therapeutic value for the treatment of diseases and conditions mediated by dysregulated activation of the classical and lectin pathways.

The invention is based on the identification of an isolated, purified peptide of 30 amino acids derived from human astrovirus coat protein, termed CP1, and having a sequence (SEQ ID NO:1) that is able to regulate the classical and lectin pathway activation by binding to C1q and MBL. In other embodiments, the peptide compounds regulate the classical pathway activation but not the lectin pathway activation.

Modifications of the amino acid structure of CP1 has led to the discovery of additional peptide compounds that are able to regulate C1q activity.

The term "peptide compound(s)," as used herein, refers to amino acid sequences, which may be naturally occurring, or peptide mimetics, peptide analogs and/or synthetic derivatives of about 30 amino acids based on SEQ ID NO:1. In addition, the peptide compound may be less than about 30 amino acid residues, such as between about 20 and about 30 amino acid residues and such as peptide compounds between about 10 to about 20 amino acid residues. Peptide residues of, for example, 5, 6, 7, 8, 9, 10, 11, 12, 13, 14, 15, 16, 17, 18, 19, 20, 21, 22, 23, 24, 25, 26, 27, 28, 29, and 30 amino acids are equally likely to be peptide compounds within the context of the present invention.

The disclosed peptide compounds are generally constrained (that is, have some element of structure as, for example, the presence of amino acids that initiate a β turn or β pleated sheet, or, for example, are cyclized by the presence of disulfide bonded Cys residues) or unconstrained (that is, linear) amino acid sequences of about 30 amino acid residues, or less than about 30 amino acid residues.

Substitutes for an amino acid within the peptide sequence may be selected from other members of the class to which the amino acid belongs. For example, the nonpolar (hydrophobic) amino acids include alanine, leucine, isoleucine, valine, proline, phenylalanine, tryptophan, and methionine. Amino acids containing aromatic ring structures include phenylalanine, tryptophan, and tyrosine. The polar neutral amino acids include glycine, serine, threonine, cysteine, tyrosine, asparagine, and glutamine. The positively charged (basic) amino acids include arginine and lysine. The negatively charged (acidic) amino acids include aspartic acid and glutamic acid. For example, one or more amino acid residues within the sequence can be substituted by another amino acid of a similar polarity, which acts as a functional equivalent, resulting in a silent alteration.

A conservative change generally leads to less change in the structure and function of the resulting protein. A non-conservative change is more likely to alter the structure, activity, or function of the resulting protein. For example, the peptide of the present disclosure comprises one or more of the following conservative amino acid substitutions: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue.

Particularly preferred amino acid substitutions include:

a) Ala for Glu or vice versa, such that a negative charge may be reduced;

b) Lys for Arg or vice versa, such that a positive charge may be maintained;

c) Ala for Arg or vice versa, such that a positive charge may be reduced;

d) Glu for Asp or vice versa, such that a negative charge may be maintained;

e) Ser for Thr or vice versa, such that a free —OH can be maintained;

f) Gln for Asn or vice versa, such that a free NH2 can be maintained;

g) Ile for Leu or for Val or vice versa, as roughly equivalent hydrophobic amino acids;

h) Phe for Tyr or vice versa, as roughly equivalent aromatic amino acids; and i) Ala for Cys or vice versa, such that disulphide bonding is affected.

In one embodiment, the invention discloses an isolated, purified peptide derived from human astrovirus coat protein, the peptide comprising the amino acid sequence of SEQ ID NO: 1.

In another embodiment, the invention discloses an isolated, purified, synthetic peptide comprising the amino acid sequence of SEQ ID NO: 1, with one or more amino acid substitutions, modifications, insertions, or deletions, wherein the peptide regulates complement activation.

In another embodiment, the invention discloses an isolated, purified, synthetic peptide comprising the amino acid sequence of SEQ ID NO: 1, with one or more conservative amino acid substitutions, wherein the peptide regulates complement activation.

The peptide compounds may have internal peptide deletions and substitutions as well as deletions and substitutions at the N-terminus and C-terminus based on SEQ ID NO:1. In some embodiments, the peptide has about 1, 2, 3, 4, 5, 6, 7, 8, 9, 10, 15, or 20 or more amino acid substitutions, modifications, insertions, or deletions.

In some embodiments, the peptide sequence has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO:1.

Astrovirus Coat Protein Peptides and Derivatives

Figures 2A, 2B:
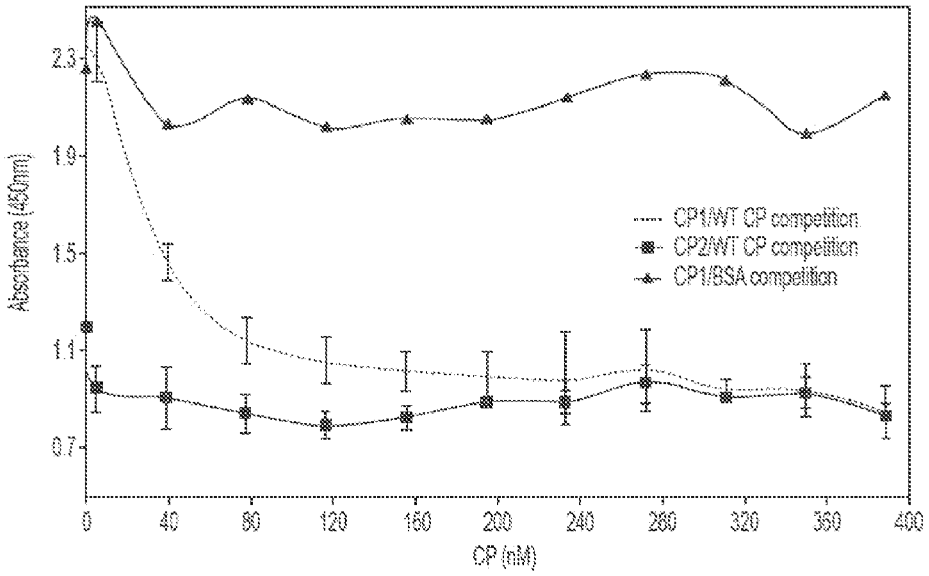
FIG. 2A shows the alignment of WT CP with the 30 amino acid HNP-1 molecule as determined by ClustalW analysis. The symbol "*" indicates identical residues, ":" indicates conserved residues, and "." indicates semi-conserved residues between CP and HNP-1 sequences.
FIG. 2B is a graph depicting peptide compounds that dose-dependently competed with WT CP for C1q binding. A constant amount of C1q was mixed with increasing amounts of WT CP and added to an ELISA plate coated with CP1 (no symbol) or CP2 (squares). When BSA was substituted for WT CP (triangles), no competition occurred. Data are the means from three independent experiments. Error bars denote SEM.

Two 30-residue peptides that encompassed the region of homology between HNP-1 and the WT CP, CP1 and CP2, were synthesized (FIG. 2A). CP1 demonstrated consistent regulation of classical pathway activation, while CP2 did not regulate classical pathway activation. CP1 retains limited homology with HNP-1 at its N and C termini (four residues each); however, no homology exists internally to these flanking residues, as shown in FIG. 2A. While not bound by any theory, WT CP may regulate C1 and MBL activity by binding the collagen-like regions of both molecules and dissociating their associated serine proteases, C1s-C1r-C1r-C1s and MASP2, from C1q and MBL, respectively (Hair et al., 2010. *Molec. Immunol.* 47, 792-798).

The peptide compounds in this disclosure were synthesized through peptide deletions and substitutions of CP1, the 30 amino acid peptide of HAstV CP described above. Additional peptide compounds have been synthesized based on modifications of CP1, as shown in TABLE 1 below.

TABLE 1

| Peptide | Peptide sequence (N→C) |
|---|---|
| CP2 | NPVLVKDATGSTQFG PVQALGAQYSMWKLK (SEQ ID NO: 2) |
| CP1 | PAICQRATATLGTVG SNTSGTTEIEACILL (SEQ ID NO: 1) |
| C04A | PAI**A**QRATATLGTVG SNTSGTTEIEACILL (SEQ ID NO: 3) |
| C27A | PAICQRATATLGTVG SNTSGTTEIEA**A**ILL (SEQ ID NO: 4) |
| E23A | PAICQRATATLGTVG SNTSGTT**A**IEACILL (SEQ ID NO: 5) |
| E25A | PAICQRATATLGTVG SNTSGTTEI**A**ACILL (SEQ ID NO: 6) |
| Δ8-22 | PAICQRA-------- -------EIEACILL (SEQ ID NO: 7) |
| Δ8-22 oxidized | PAICQRA-------- -------EIEACILL (SEQ ID NO: 7) |
| Δ8-22 Abu | PAIaQRA-------- -------EIEAaILL (SEQ ID NO: 8) |
| Polar Assortant | IALILEPICCQERAA (SEQ ID NO: 9) |

CP1 is an isolated, purified peptide derived from human astrovirus coat protein, the peptide comprising an amino acid sequence of SEQ ID NO: 1.

CP2 is an isolated, purified peptide derived from human astrovirus coat protein, the peptide comprising an amino acid sequence of SEQ ID NO: 2.

Figure 3A:
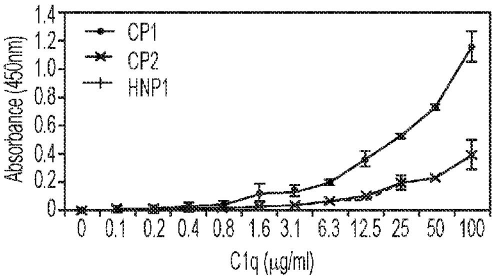
FIGS. 3A-3D demonstrates the binding of CP peptides to C1q. Peptides CP1, CP2, HNP-1 (FIG. 3A), C04A, C27A (FIG. 3B), E23A, E25A (FIG. 3C) and Δ8-22 (FIG. 3D) were coated onto the ELISA plate and incubated with increasing amounts of purified C1q. C1q was detected with polyclonal antisera to C1q. Data represents triplicate readings for each peptide derivative. Error bars denote SEM.

Using CP1 as the parent peptide, four alanine substitutions (C04A, C27A, E23A, E25A) were made (alanine-substituted residues are in bold and underlined in TABLE 1). Internal deletions of residue 8 to residue 22 were made for the Δ8-22 peptide (internal deletions are shown as dashes in TABLE 1). CP2, CP1, and CP1 derivatives were coated on a plate. After blocking, increasing amounts of C1q was added for 1 hour at room temperature, followed by detection of C1q with antisera to C1q. Binding of C1q by the various peptide derivatives is shown in FIG. 3. Data represents triplicate readings for each peptide compound. CP1 bound C1q in a dose-dependent manner (FIG. 3A). While CP2 bound less C1q than CP1, it bound C1q at similar levels to that of HNP-1 (FIG. 3A).

Figure 5:
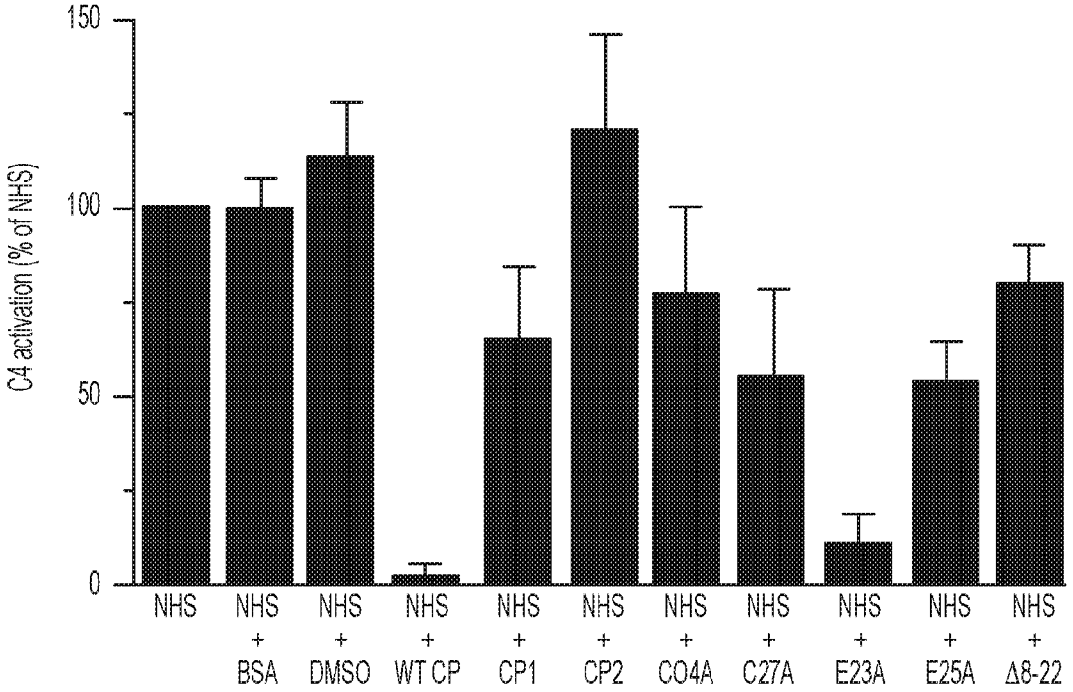
FIG. 5 is a graph depicting peptide compound regulation of complement activity in a C4 activation assay. ELISA plates were pre-coated with ovalbumin decorated with anti-ovalbumin antibodies. NHS was incubated alone or with BSA, dimethyl sulfoxide (DMSO) control, WT CP (1.8 μg), or peptide compounds (0.5 mM) for 15 minutes and subsequently added to the ovalbumin-antibody target. Polyclonal C4 antibody was used to detect C4 deposition. C4 deposition was standardized to 100% for NHS alone, and all values were adjusted to subtract out background values from a heat-inactivated NHS control. Data are the means from three independent experiments. Error bars denote SEM.
Figure 6A:
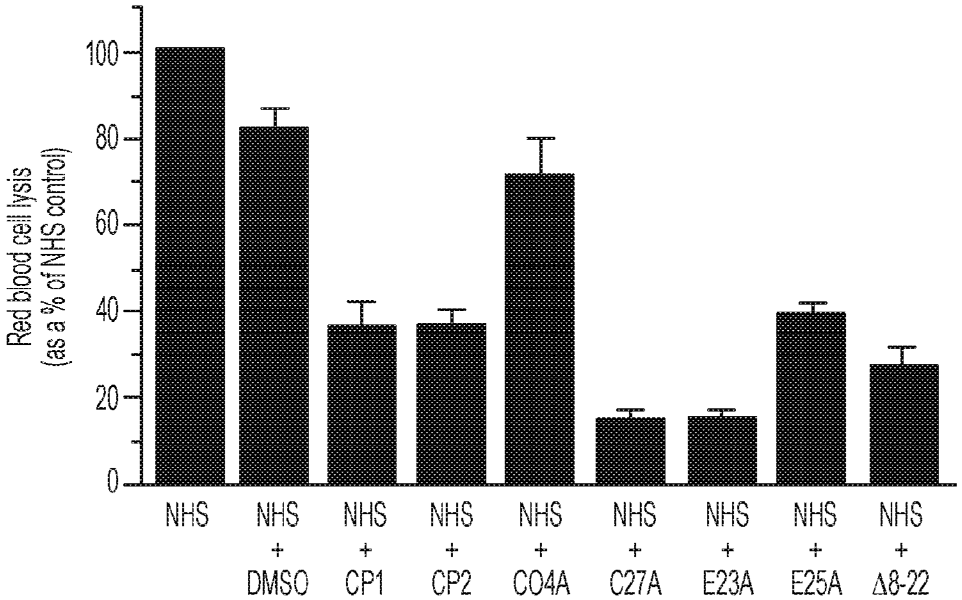
FIGS. 6A and 6B are graphs depicting peptide compound regulation of complement activity in a hemolytic assay.
Figure 6B:
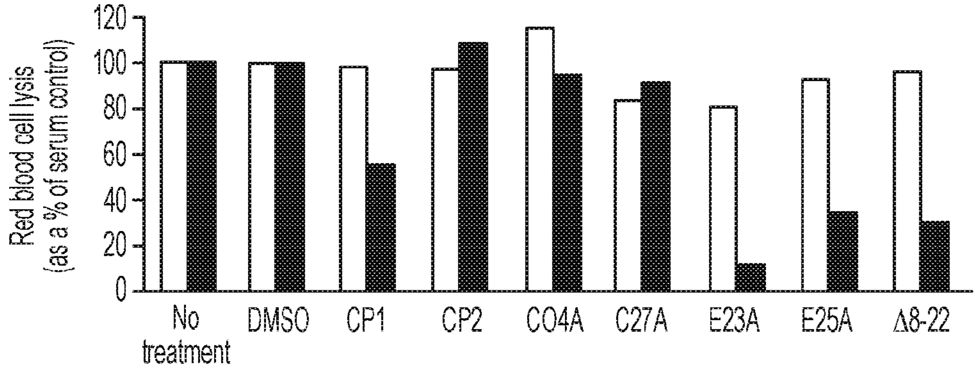
Figures 9A, 9B:
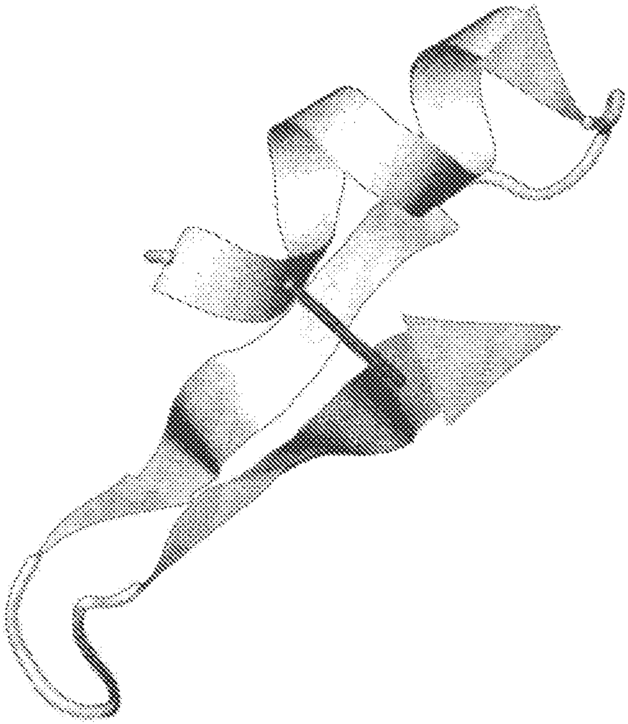
FIG. 9A depicts the amino acid residues of E23A compared to the residues of *Vigna radiata* plant defensin 1 (VrD1). E23A was uploaded onto CPHModels-3.0 server, which aligned residues 2-29 of E23A with residues 17-44 of the plant defensin VrD1. The alignment was confirmed by ClustalW analysis. The symbol "*" indicates identical residues, ":" indicates conserved residues, and "." indicates semi-conserved residues.
FIG. 9B is an image depicting the structural model of E23A. The PDB coordinates generated by CPHModels-3.0 were uploaded onto FirstGlance in Jmol to visualize the structural model. The N-terminal alpha helix and beta strands are shown as ribbons, with arrowheads pointing towards the carboxy termini. Random coil is shown as smoothed backbone traces. The putative disulphide bond is shown as a thin cylinder.

As shown in TABLE 1, CP1 contains two cysteine residues at positions 4 and 27, which were individually substituted with alanine in C04A and C27A. The cysteine residues of CP1 were targeted to determine if disulphide bonding in CP1 is required for classical pathway activation. As is known in the art, the peptide regulators of C3 (Compstatin) and C1q (peptide 2J), both of which contain two cysteine residues in their amino acid sequences, require cyclicalization through disulphide bonding for activity (Sahu et al., 1996. *J. Immunol.* 157, 884-891; Roos et al., 2001. *J. Immunol.* 167, 7052-7059). The cysteine substitutions had no significant effects on C1q binding (FIG. 3B) or C4 activation (FIG. 5). However, both cysteine substitutions demonstrated loss of complement regulatory activity in the hemolytic assays (FIG. 6B). This suggests that although cyclicalization via disulphide bonding of the cysteine residues is not critical for C1q binding, cyclicalization appears to have a variable effect on their ability to inhibit activation of the complement system. Thus, while not bound by any theory, disulphide bonding of the cysteine residues may be important for proper peptide conformation and stability, as suggested by the structural model of E23A (FIG. 9B).

As shown in TABLE 1, glutamic acid residues at positions 23 and 25 were also substituted with alanine. Substitution of the glutamic acid residues was performed because these negatively charged amino acids may play a role in CP interaction with non-hydroxylated lysine residues on the C1q molecule. E23A and E25A peptides demonstrated efficient binding to C1q (FIG. 3C) and similar or greater regulatory activity than CP1 in all functional assays (FIGS. 5 and 6). In particular, E23A showed superior regulation of classical pathway activation in comparison to all the other peptide derivatives tested. It appears that substitution of one of the negatively charged glutamic acid by the neutral alanine residue enhances the peptide's regulatory activity.

Figure 3B:
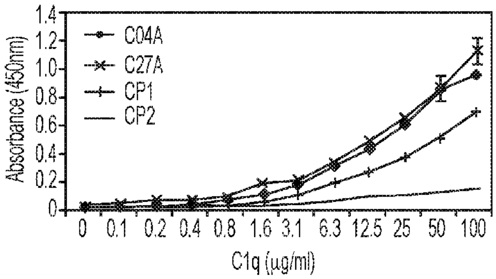
Figure 3C:
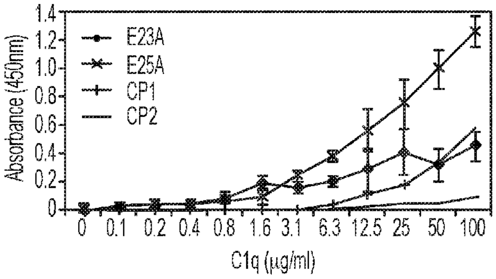
Figure 3D:
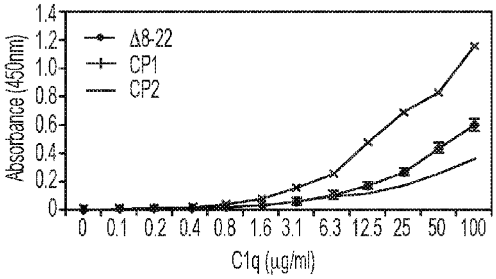

As shown in TABLE 1, the Δ8-22 peptide was a deletion of residues 8-22 from E23A. This peptide was active in all functional assays tested and bound C1q (FIG. 3D). This Δ8-22 peptide retains the two cysteine and two glutamic acid residues and is half the size of CP1 (15 residues versus 30 residues).

The Δ8-22 peptide (SEQ ID No. 7) was oxidized during synthesis to form a disulphide bond between the two cysteine residues (Δ8-22 oxidized). This peptide was active in all functional assays tested. The two cysteine residues were replaced in the Δ8-22 peptide with a cysteine derivative that does not form a disulphide bond, such that the peptide stays reduced. (Δ8-22 peptide Abu; SEQ ID No. 8). This peptide was active in all functional assays tested. With the peptide Polar Assortant (SEQ ID No. 9), the 15 amino acid residues from Δ8-22 peptide were scrambled. This peptide was also active in all functional assays tested.

Rational Peptide Deletions, Substitutions, and Modifications

A series of peptide deletions, substitutions, and modifications of CP1 are disclosed, as shown in TABLE 2 below. The subject matter discloses an isolated, purified, synthetic peptide comprising any one of the amino acid sequences of SEQ ID NOs: 1-35, as shown in TABLES 1 and 2.

TABLE 2

| Peptide | | |
|---|---|---|
| | **Astrovirus CP1** | |
| | PAICQRATATLGTVGSNTSGTTEIEACILL | (SEQ ID NO: 1) |
| | **Internal deletions** | |
| | PAICQRATATLGT---NTSGTTEIEACILL | (SEQ ID NO: 10) |
| | PAICQRATATL-------SGTTEIEACILL | (SEQ ID NO: 11) |
| | PAICQRATA-----------TTEIEACILL | (SEQ ID NO: 12) |
| Δ8-22 | PAICQRA---------------EIEACILL | (SEQ ID NO: 7) |
| | **N-terminal deletions** | |
| | -AICQRATATLGTVGSNTSGTTEIEACILL | (SEQ ID NO: 13) |
| | --ICQRATATLGTVGSNTSGTTEIEACILL | (SEQ ID NO: 14) |
| | ---CQRATATLGTVGSNTSGTTEIEACILL | (SEQ ID NO: 15) |
| | **C-terminal deletions** | |
| | PAICQRATATLGTVGSNTSGTTEIEACIL- | (SEQ ID NO: 16) |
| | PAICQRATATLGTVGSNTSGTTEIEACI-- | (SEQ ID NO: 17) |
| | PAICQRATATLGTVGSNTSGTTEIEAC--- | (SEQ ID NO: 18) |
| | **N- and C-terminal deletions** | |
| CP1, aa 8-22 | TATLGTVGSNTSGTT | (SEQ ID NO: 19) |
| CP2, aa 9-23 | TGSTQFGPVQALGAQ | (SEQ ID NO: 20) |
| | **Alanine scan including the following specific substitutions** | |
| C04A | PAI**A**QRATATLGTVGSNTSGTTEIEACILL | (SEQ ID NO: 3) |
| C27A | PAICQRATATLGTVGSNTSGTTEIEA**A**ILL | (SEQ ID NO: 4) |
| C04,27A | PAI**A**QRATATLGTVGSNTSGTTEIEA**A**ILL | (SEQ ID NO: 21) |
| E23A | PAICQRATATLGTVGSNTSGTT**A**IEACILL | (SEQ ID NO: 5) |
| E25A | PAICQRATATLGTVGSNTSGTTEI**A**ACILL | (SEQ ID NO: 6) |
| E23,25A | PAICQRATATLGTVGSNTSGTT**A**I**A**ACILL | (SEQ ID NO: 22) |
| E23A, Δ8-22 | **A**AICQRA---------------EIEACILL | (SEQ ID NO: 23) |
| E23A, Δ8-22 | PA**A**CQRA---------------EIEACILL | (SEQ ID NO: 24) |
| E23A, Δ8-22 | PAI**A**QRA---------------EIEACILL | (SEQ ID NO: 25) |
| E23A, Δ8-22 | PAIC**A**RA---------------EIEACILL | (SEQ ID NO: 26) |
| E23A, Δ8-22 | PAICQ**A**A---------------EIEACILL | (SEQ ID NO: 27) |
| E23A, Δ8-22 | PAICQRA---------------**A**IEACILL | (SEQ ID NO: 28) |
| E23A, Δ8-22 | PAICQRA---------------E**A**EACILL | (SEQ ID NO: 29) |
| E23A, Δ8-22 | PAICQRA---------------EI**A**ACILL | (SEQ ID NO: 30) |
| E23A, Δ8-22 | PAICQRA---------------EIEA**A**ILL | (SEQ ID NO: 31) |

TABLE 2-continued

| Peptide | | |
|---|---|---|
| E23A, Δ8-22 | PAICQRA---------------EIEAC**A**LL | (SEQ ID NO: 32) |
| E23A, Δ8-22 | PAICQRA---------------EIEACI**A**L | (SEQ ID NO: 33) |
| E23A, Δ8-22 | PAICQRA---------------EIEACIL**A** | (SEQ ID NO: 34) |
| | N-terminal acetylation | |
| | Ac PAICQRATATLGTVGSNTSGTTEIEACILL | (SEQ ID NO: 35) |

Internal Deletions

As described above, CP1 is 30 amino acid residues in length and aligns with the first ten residues of HNP-1, as shown in FIG. 2A. Alignment of these two molecules was based upon the cysteine residues at the N and C terminus that are required for cyclicalization of CP1. This led to an 18-residue internal region of CP1 that shares no sequence homology with HNP-1. Increasingly large internal deletions of CP1 are synthesized and evaluated for C1q and MBL binding (TABLE 2, Internal deletions).

N- and C-Terminal Deletions

As shown in TABLE 2 (N- and C-terminal deletions), the N and C terminal amino acids are progressively deleted individually up to each cysteine residue of CP1. Additionally, both N- and C-terminal deletions from CP1 and CP2 are made to create 15 amino acid peptides. These modified peptide compounds are synthesized and evaluated for C1q and MBL binding to determine if these flanking residues are required for C1q and MBL binding activity. These deletions assist in determining the minimal size of the peptide compound required for regulating complement activation.

Alanine Scan

Alanine scanning is done to identify specific amino acid residues that are responsible for a peptide's activity. With alanine scanning, alanine is used to substitute each residue sequentially. The substitution of an essential amino acid results in a change in peptide activity, with the degree of activity taken as a relative measure of the importance of the amino acid being substituted.

The subject matter discloses peptide compounds substituted with alanine at certain positions. The subject matter discloses an isolated, purified, synthetic peptide comprising the sequence of SEQ ID NO:1, wherein one or more of the amino acids are substituted with alanine, wherein the peptide regulates complement activation. In one or more embodiments, the amino acids substituted with alanine are at positions 4, 23, 25, or 27.

Two glutamic acid residue positions are substituted both individually and together with alanine (TABLE 2, in bold and underlined). While not bound by any theory, the wild-type CP molecule may interact with reactive lysine residues on C1q and MBL that are required for binding the serine proteases C1s-C1r-C1r-C1s and MASP2, respectively. Given the negative charge associated with glutamic acid, these residues may interact directly with the positively charged lysine residues on C1q and MBL to facilitate CP binding. Two cysteine residue positions, both individually and together, are substituted with alanine (TABLE 2, in bold and underlined).

N-Terminal Acetylation

The subject matter discloses peptide compounds with acetylation of the N terminus. Acetylation of CP1 increases potency by reducing the charge at the N terminus of the peptide (i.e., electrostatic effects) (Ricklin and Lambris, 2008. Nat. Biotech. 25, 1265-1275). This modification may aid in improving the in vivo stability of the peptide with respect to exopeptidases, as was shown with Compstation (Ricklin and Lambris, 2008. *Nat. Biotech.* 25, 1265-1275). The peptide compound synthesized from N-terminal acetylation includes any of the peptides described above, wherein the peptide is modified through acetylation of the N-terminal residue.

The Complement System and Diseases Associated with its Dysregulation

While complement is a vital host defense against pathogenic organisms such as bacteria and some enveloped viruses, its unchecked activation can cause devastating host cell damage. Host tissue damage mediated by complement has been implicated in a wide variety of diseases, including autoimmune pathologies such as: rheumatoid arthritis, systemic lupus erythematosus, multiple sclerosis, myasthenia gravis, autoimmune hemolytic anemia, membranoproliferative glomerulonephritis, and serum sickness. It has also been identified as contributing to the pathogenesis of the following diseases: Adult Respiratory Distress Syndrome (ARDS), ischemia-reperfusion injuries (including stroke and myocardial infarction), allo- and xeno-transplantation complications (including hyperacute rejection and graft versus host disease (GVHD)), Alzheimer's disease, burn injuries, hemodialysis damage, cardiopulmonary bypass damage, and paroxysmal nocturnal hemoglobinuria (PNH).

Hereditary angioedema (HAE) is a very rare genetic disorder caused by reduced levels of or non-functional C1-inhibitor; symptoms of HAE include acute edema. C1-inhibitor naturally regulates C1 activation, and treatment of acute edema requires substantial infusion of C1-inhibitor or plasma transfusion. Because astrovirus CP functionally blocks C1 activation, using the disclosed peptide compounds to treat HAE fulfills a therapeutic need because C1-inhibitor has to be purified from human sera from multiple subjects and, therefore, could be contaminated with human blood-borne pathogens. Therapeutic administration of the disclosed peptide compounds regulates C1 either in adjunct therapy with C1-inhibitor or as a stand-alone therapeutic treatment.

The disclosed peptide compounds can selectively regulate C1q and MBL activation without affecting alternative pathway activity and are, thus, ideal for preventing and treating diseases mediated by the dysregulated activation of the classical and lectin pathways. The alternative pathway is essential for immune surveillance against invading pathogens, and humans with alternative pathway defects suffer severe bacterial infections. By binding and inactivating C1q and MBL, the peptide compounds can efficiently regulate classical and lectin pathway activation while leaving the alternative pathway intact.

The term "regulate," as used herein, refers to i) controlling, reducing, inhibiting or regulating the biological function of an enzyme, protein, peptide, factor, byproduct, or derivative thereof, either individually or in complexes; ii)

reducing the quantity of a biological protein, peptide, or derivative thereof, either in vivo or in vitro; or iii) interrupting a biological chain of events, cascade, or pathway known to comprise a related series of biological or chemical reactions. The term "regulate" may thus be used, for example, to describe reducing the quantity of a single component of the complement cascade compared to a control sample, reducing the rate or total amount of formation of a component or complex of components, or reducing the overall activity of a complex process or series of biological reactions, leading to such outcomes as cell lysis, formation of convertase enzymes, formation of complement-derived membrane attack complexes, inflammation, or inflammatory disease. In an in vitro assay, the term "regulate" may refer to the measurable change or reduction of some biological or chemical event, but the person of ordinary skill in the art will appreciate that the measurable change or reduction need not be total to be "regulatory."

Pharmaceutical Formulation and Administration

The present disclosure provides pharmaceutical compositions capable of regulating the complement system, comprising at least one peptide compound, as discussed above, and at least one pharmaceutically acceptable carrier, diluent, or excipient. Pharmaceutically acceptable carriers, excipients, or stabilizers are nontoxic to recipients at the dosages and concentrations employed. They can be solid, semi-solid, or liquid. The pharmaceutical compositions of the present invention can be in the form of tablets, pills, powders, lozenges, sachets, cachets, elixirs, suspensions, emulsions, solutions, or syrups.

Some examples of pharmaceutically acceptable carriers, diluents, or excipients include: lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The pharmaceutical compositions of the present invention can be formulated using procedures known in the art to provide quick, normal, or sustained or delayed release of the active ingredient.

The disclosure relates to a method of regulating the complement system in a subject comprising administering to a subject the compositions described above. The pharmaceutical compositions of the present invention are prepared by mixing the peptide compound having the appropriate degree of purity with pharmaceutically acceptable carriers, diluents, or excipients. Examples of formulations and methods for preparing such formulations are well known in the art. The pharmaceutical compositions of the present invention are useful as a prophylactic and therapeutic agent for various disorders and diseases, as set forth above. In one embodiment, the composition comprises a therapeutically effective amount of the peptide compound. In another embodiment, the composition comprises at least one other active ingredient effective in treating at least one disease associated with complement-mediated tissue damage. The term "therapeutically effective amount," as used herein, refers to the total amount of each active component that is sufficient to show a meaningful benefit to the subject.

The term "subject," as used herein, means any subject for whom diagnosis, prognosis, or therapy is desired. For example, a subject can be a mammal, e.g., a human or non-human primate (such as an ape, monkey, orangutan, or chimpanzee), a dog, cat, guinea pig, rabbit, rat, mouse, horse, cattle, or cow.

As used herein, "treat," "treating," or "treatment" refers to administering a therapy in an amount, manner (e.g., schedule of administration), and/or mode (e.g., route of administration), effective to improve a disorder (e.g., a disorder described herein) or a symptom thereof, or to prevent or slow the progression of a disorder (e.g., a disorder described herein) or a symptom thereof. This can be evidenced by, e.g., an improvement in a parameter associated with a disorder or a symptom thereof, e.g., to a statistically significant degree or to a degree detectable to one skilled in the art. An effective amount, manner, or mode can vary depending on the subject and may be tailored to the subject. By preventing or slowing progression of a disorder or a symptom thereof, a treatment can prevent or slow deterioration resulting from a disorder or a symptom thereof in an affected or diagnosed subject.

The therapeutically effective amount of the peptide compound varies depending on several factors, such as the condition being treated, the severity of the condition, the time of administration, the route of administration, the rate of excretion of the compound employed, the duration of treatment, the co-therapy involved, and the age, gender, weight, and condition of the subject, etc. One of ordinary skill in the art can determine the therapeutically effective amount. Accordingly, one of ordinary skill in the art may need to titer the dosage and modify the route of administration to obtain the maximal therapeutic effect.

The effective daily dose generally is within the range of from about 0.001 to about 100 milligrams per kilogram (mg/kg) of body weight, preferably about 0.01 to about 50 mg/kg, more preferably about 0.1 to about 20 mg/kg. This dose can be achieved through a 1-6 time(s) daily dosing regimen. Alternatively, optimal treatment can be achieved through a sustained release formulation with a less frequent dosing regimen.

Pharmaceutical formulations may be adapted for administration by any appropriate route, for example, by the oral, nasal, topical (including buccal, sublingual, or transdermal), or parenteral (including subcutaneous, intracutaneous, intramuscular, intraarticular, intraperitoneal, intrasynovial, intrasternal, intrathecal, intralesional, intravenous, or intradermal injections or infusions) route. For human administration, the formulations preferably meet sterility, pyrogenicity, general safety, and purity standards, as required by the offices of the Food and Drug Administration (FDA).

Combination Therapies

A further embodiment of the invention provides a method of preventing or treating a disease associated with complement-mediated tissue damage, comprising administering to a subject the pharmaceutical compositions of the present invention. While the pharmaceutical compositions of the present invention can be administered as the sole active pharmaceutical agent, they can also be used in combination with one or more therapeutic or prophylactic agent(s) that is(are) effective for preventing or treating the disease. In this aspect, the method of the present invention comprises administrating the pharmaceutical composition of the present invention before, concurrently, and/or after one or more additional therapeutic or prophylactic agents effective in treating at least one disease associated with complement-mediated tissue damage.

For example, the pharmaceutical compositions of the present invention can be used to treat rheumatoid arthritis, either alone or in combination with a non-steroidal anti-inflammatory agent (NSAID), a corticosteroid, or a disease modifying anti-rheumatic drug (DMARD).

Examples of NSAIDs include: salicylates (such as aspirin, amoxiprin, benorilate, choline magnesium salicylate, diflunisal, faislamine, methyl salicylate, magnesium salicylate, and salicyl salicylate (salsalate)), arylalkanoic acids (such as diclofenac, aceclofenac, acemetacin, bromfenac, etodolac, indometacin, ketorolac, nabumetone, sulindac, and tolmeti), 2-arylpropionic acids (such as ibuprofen, carprofen, fenbufen, fenoprofen, flurbiprofen, ketoprofen, loxoprofen, naproxen, tiaprofenic acid, and suprofen), N-arylanthranilic acids (such as mefenamic acid and meclofenamic acid), pyrazolidine derivatives (such as phenylbutazone, azapropazone, metamizole, oxyphenbutazone, and sulfinprazone), oxicams (such as piroxicam, lornoxicam, meloxicam, and tenoxicam), COX-2 inhibitors (such as etoricoxib, lumiracoxib, and parecoxib), sulphonanilides such as nimesulide, and others such as licofelone and omega-3 fatty acids.

Examples of corticosteroid include: triamcinolone (Aristocort®), cortisone (Cortone® Acetate Tablets), dexamethasone (Decadron® Elixir), prednisone (Deltasone®), and methylprednisolone (Medrol®).

Examples of DMARD include: methotrexate (Rheumatrex®), leflunomide (Arava®), etanercept (Enbrel®), infliximab (Remicade®), adalimumab (Humira®), anakinra (Kineret®), sulfasalazine (Azulfidine EN-Tabs®), antimalarials, gold salts, d-penicillamine, cyclosporin A, cyclophosphamide and azathioprine.

Soliris™ (eculizumab) is a humanized anti-05 monoclonal antibody. It has been approved by the FDA for the treatment of the rare form of hemolytic anemia, paroxysmal nocturnal hemoglobinuria. In one embodiment, the pharmaceutical compositions of the present invention can be used in combination with Soliris™ in treating paroxysmal nocturnal hemoglobinuria, heart disease, pulmonary diseases, autoimmune diseases, asthma, as well as the ancillary care of transplants.

The pharmaceutical compositions of the present invention can be administered with the additional agent(s) in combination therapy, either jointly or separately, or by combining the pharmaceutical compositions and the additional agent(s) into one composition. The dosage is administered and adjusted to achieve maximal management of the conditions. For example, both the pharmaceutical compositions and the additional agent(s) are usually present at dosage levels of between about 10% and about 150%, more preferably, between about 10% and about 80%, of the dosage normally administered in a mono-therapy regimen.

EXAMPLES

The invention is further illustrated by the following examples, provided for illustrative purposes only. They are not to be construed as limiting the scope or content of the invention in any way.

Materials and Methods

Example 1—Preparation of HAstV-1 CP, Peptides, Heat-aggregated IgG, Sera, Erythrocytes, and Complement Buffers Wild-type HAstV-1 CP was expressed from a recombinant baculovirus in *Spodoptera frugiperda* cells (line IPLB-Sf21) and purified as previously described (Bonaparte et al., 2008. *J. Virol.* 82, 817-827). HNP-1, CP1, and CP2 peptides were obtained from Biomatik, whereas C04A, C27A, E23A, E25A and d8-22 were purchased from GenScript. Before shipment, the peptide compounds were analyzed by HPLC and ESI-mass spectrometry. Upon receipt, peptides were dissolved in dimethylsulfoxide (DMSO) at a concentration of 10 mM and stored at −80° C. Heat-aggregated human IgG was prepared using methods known in the art (Bonaparte et al., 2008. *J. Virol.* 82, 817-827). Pooled normal human serum (NHS) was derived from the blood of healthy human volunteers according to an Institutional Review Board approved protocol (IRB 02-06-EX-0216, Eastern Virginia Medical School) and was pooled, aliquoted, and frozen at −80° C. using methods known in the art (Cunnion et al., 2001. *Infect. Immun.* 69, 6796-6803). Antibody-sensitized sheep erythrocytes were generated using methods known in the art (Bonaparte et al., 2008. *J. Virol.* 82, 817-827). Standard complement buffers were used: $GVBS^{++}$ (Veronal-buffered saline, 0.1% gelatin, 0.15 mM $CaCl_2$, and 1.0 mM $MgCl_2$) and $GVBS^{--}$ (Veronal-buffered saline, 0.1% gelatin, 0.01 M EDTA).

Example 2—C1q ELISA Protocols for WT CP and Peptide Compounds

To analyze whether CP competes with HNP-1 for C1q binding, HNP-1 peptides (2.5 μM) were coated onto 96-well Maxisorp plates (Nunc) in coating buffer (100 mM $Na_2CO_3$, $NaHCO_3$, [pH 9.6]) and plates were incubated at room temperature overnight. Plates were washed with PBS/T and blocked with 3% BSA/PBS, 0.05% Tween-20 (PBS/T) for 2 hours at room temperature. Next, a constant amount of purified C1q (10 μg/ml; Complement Technologies, Inc.) was added to each well, while decreasing amounts of CP, starting at 100 μg/mL, were added simultaneously and incubated for 1 hour at room temperature. BSA was substituted for CP as a negative control for competition. After washing, the primary antibody, goat anti-C1q polyclonal antibody (Complement Technologies, Inc.), was diluted 1:2,000 in 3% BSA/PBS/T and added to the plate for 1 hour at room temperature. The plate was washed and the secondary antibody, donkey anti-goat HRP (Santa Cruz Biotechnology, Inc.), was diluted 1:2,500 in 3% BSA/PBS/T and incubated for 1 hour at room temperature. The plates were washed with PBS/T and developed with tetramethyl benzindine (Sigma) for 1 min. The reactions were then stopped with 0.1 ml 1N $H_2SO_4$ and absorbance was read in a Synergy HT plate reader (Bio-Tek Instruments) at a wavelength of 450 nm. To assess competitive binding of CP peptides CP1 and CP2 for C1q binding, the assay was carried out in an identical manner to that described above, except CP1 and CP2 were coated onto plates (2.5 μM) and BSA was used in parallel with CP as a negative control for competition.

To determine the binding of CP peptide derivatives to C1q, peptides at 2.5 μM were coated on the plate and incubated overnight at room temperature. After washing and blocking, decreasing amounts of C1q, starting at 100 μg/mL, were added to the wells and incubated for 1 hour at room temperature. C1q was detected and the plates developed as described above.

Example 3—C1s Immunoblot

One μl of partially purified human C1 (0.2 mg/ml, Complement Technologies, Inc.) was incubated at 37° C. for 90 minutes, either alone or with heat-aggregated human immunoglobulin G (5 μl of a 1:250 dilution of 50 μg/ml starting solution), or with increasing amounts of the indicated peptides (250 μM stock), and brought up to a total volume of 11 μl in PBS. After the incubation, an equal volume of loading buffer was added to all samples, which were subsequently boiled and electrophoresed through an 8% SDS-PAGE for 60 minutes at 140 volts. The gel was then transferred to nitrocellulose and blocked with non-fat dried milk (NFDM) in PBS. The blot was probed with a goat polyclonal antibody to C1s (Quidel) at a 1:2,000 dilution, washed in PBS/0.1% Tween-20, followed by HRP-conjugated donkey anti-goat IRDye 680 antibody (Li-cor Biosciences) at a 1:10,000 dilution and washed with PBS/0.1% Tween. The blot was then imaged on an Odyssey imager using version 3.0 software (Li-cor Biosciences), and activation of C1s was determined from the amounts of the C1s heavy and light chains characteristic of activated C1s relative to the proenzyme species.

Example 4—C4 Activation Assay

The C4 activation assay was adapted from Mallik et al., 2005. *J. Med. Chem.* 48, 274-286. Wells of Immulon-2, 96 well plates were coated with 50 μl of 1.0 mg/ml ovalbumin (Fisher) in coating buffer and incubated overnight at 4° C. The plates were washed with PBS/T and blocked with 3% BSA/PBS for 2 hours at room temperature. The plates were washed again and then incubated with a rabbit anti-ovalbumin antibody (Millipore) diluted in 3% BSA/PBS at 1:2,000 for 1 hour at room temperature. During this incubation, the peptides were diluted to 0.5 mM in 10% NHS/$GVBS^{++}$ and incubated for 15 minutes at 37° C. The plates were then washed, and the pre-incubated samples were added to the plates at a 1:4 dilution in $GVBS^{++}$ and incubated for 30 minutes at room temperature. Afterwards, the plates were washed and goat anti-C4 antibody (Complement Technologies, Inc.) was added at a dilution of 1:2,000 in 3% BSA/PBS for 1 hour, followed by another wash and a donkey anti-goat IgG-HRP antibody (Santa Cruz Biotechnology, Inc.) diluted to 1:2,000 in 3% BSA/PBS for 1 hour. The plates were then developed and absorbance values determined as described above.

Example 5—Hemolytic Assay

Peptides were diluted to 1.4 mM or 0.77 mM in undiluted NHS or factor B-depleted human sera (Complement Technologies, Inc.) and incubated for 1 hour at 37° C. These peptides were then diluted with $GVBS^{++}$ to equal 2.5/0 NHS, of which 0.25 ml was combined with 0.4 ml of $GVBS^{++}$ and 0.1 ml of sensitized sheep red blood cells (RBCs) and again incubated for 1 hour at 37° C. The procedure was stopped by the addition of 4.0 ml of $GVBS^{--}$, centrifuged for 5 minutes at 1,620×g, and the absorbance of the supernatants was read at 412 nm in a spectrophotometer. The percent lysis of each sample was standardized to that of the NHS only control.

Figure 7:
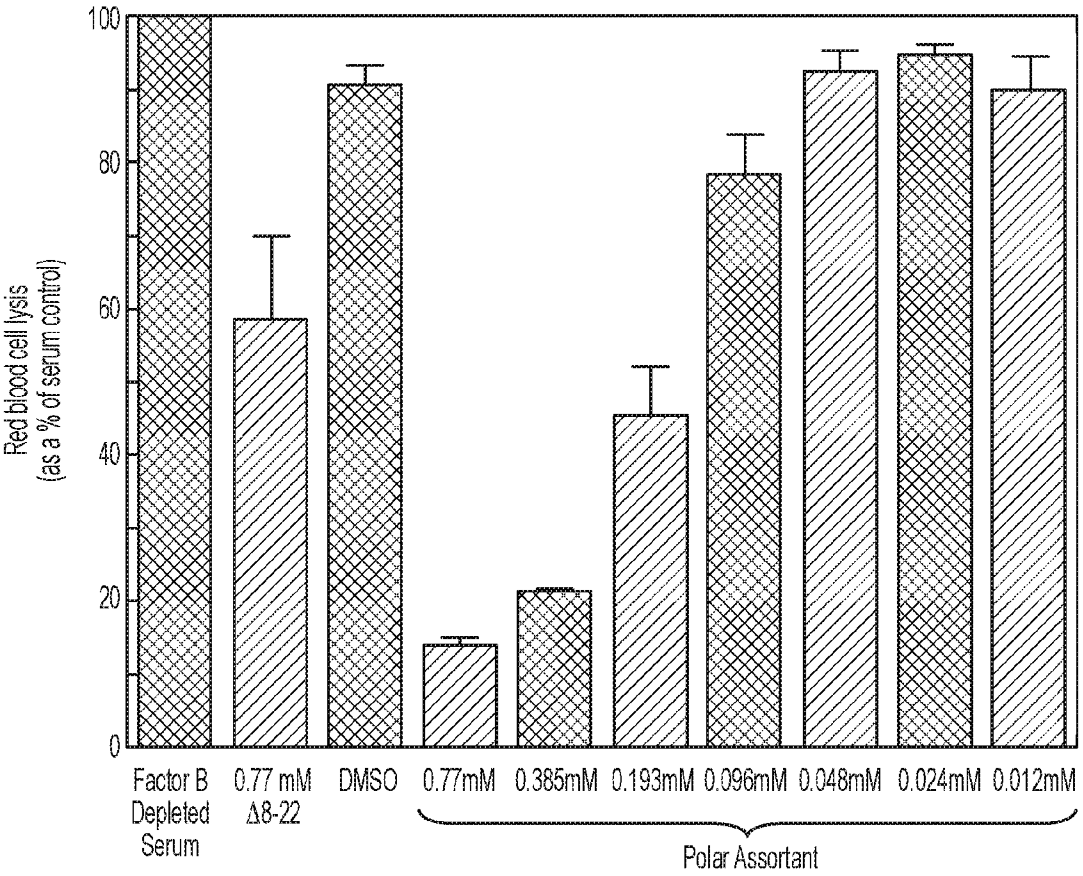
FIG. 7 is a graph depicting the hemolytic assay titration of the Polar Assortant peptide in Factor B-depleted serum. The data shows the Polar Assortant peptide regulating classical pathway activation in a dose dependent manner.

Example 6—Hemolytic Assay Titration of Polar Assortant Peptide in Factor B-Depleted Serum Polar Assortant peptide was serially diluted as indicated in FIG. 7 in undiluted factor B-depleted human sera (Complement Technologies, Inc.) and incubated for 1 hour at 37° C. Factor B-depleted serum alone, 0.77 mM of Δ8-22 and DMSO were included as controls. These peptides were then diluted with $GVBS^{++}$ to equal 2.5% NHS, of which 0.25 ml was combined with 0.4 ml of $GVBS^{++}$ and 0.1 ml of sensitized sheep red blood cells (RBCs) and again incubated for 1 hour at 37° C. The procedure was stopped by the addition of 4.0 ml of $GVBS^{--}$, centrifuged for 5 minutes at 1,620×g, and the absorbance of the supernatants was read at 412 nm in a spectrophotometer. The percent lysis of each sample was standardized to that of the NHS only control.

Example 7—Statistical Analysis

For replicate experiments, means and standard errors of the mean (SEMs) were calculated using techniques known in the art (Microsoft Excel XP).

Example 8—Mass Spectrometric Analysis of Peptide Oligomerization

Synthetic peptides were purified by C18 ZipTips™ (Millipore) before mass spectrometry analysis, as follows: 10 μl of 70% acetonitrile (ACN)/0.1% triflouroacetic acid (TFA) was pipetted two times through the ZipTip to wet the resin, followed by two 10 μl washes of 0.1% TFA to equilibrate the resin. The acidified peptide sample was aspirated up and down five times through the ZipTip to bind peptides to the resin. Contaminants were washed by pipetting 0.1% TFA three times through the ZipTip before eluting the bound peptides into a fresh tube using 70% ACN/0.1% TFA. The peptides were dried in a speed vac, re-suspended in 10 μl 0.1% TFA before mixing with matrix (α-cyano-4 hydroxycinnamic acid or sinapinic acid) at a ratio of 1:4 before analysis. Mass spectrometry was performed using a Bruker Daltonics Ultraflex II™ MALDI-TOF-TOF and the data acquired in both the reflectron and linear positive modes.

Example 9—Homology Modeling of E23A Peptide

The amino acid sequence of E23A (SEQ ID NO: 5) was uploaded onto the CPHmodels 3.0 server Lund et al., 2002. Abstract at the CASP5 conference A102). The program aligned E23A with the *Vigna radiata* plant defensin 1 (VrD1), which provided the template and Protein Data Bank (PDB) coordinates for generating the structural model. The PDB coordinates for the E23A were subsequently uploaded onto FirstGlance in JMol, version 1.45 to visualize the structure.

Results

Example 10—CP Competes with HNP-1 Peptide for C1q Binding

Earlier studies have demonstrated that CP expressed as a recombinant baculovirus-expressed protein and purified from insect cell lysates can efficiently bind C1q and MBL with resultant inhibition of the classical and lectin complement pathways (Bonaparte et al., 2008, Hair et al., 2010). Previously, it was shown that the peptide human neutrophil defensin-1 (HNP-1) can bind C1q and MBL, regulating activation of the classical and lectin pathways of complement, respectively (van den Berg et al., 1998. *Blood.* 92, 3898-3903; Groeneveld et al., 2007. *Molec. Immunol.* 44, 3608-3614). Given that CP also possesses these properties, the amino acid sequences of both proteins were analyzed and a region of limited homology found between HNP-1 and residues 79-139 of the WT CP. Then, it was analyzed whether CP could directly compete with HNP-1 for binding to C1q using a competition ELISA approach in which HNP-1 peptide was coated on the ELISA plate. FIG. 1 is a graph depicting CP dose-dependently competing with human neutrophil defensin 1 (HNP-1) for binding to C1q. A fixed amount of purified C1q and increasing amounts of CP were added simultaneously. Adherent C1q bound to HNP-1 was detected with polyclonal antibody to C1q. Bound C1q signal decreased with increasing amounts of CP, indicating that CP dose-dependently competes with HNP-1 for C1q binding (FIG. 1, shown as circles). In contrast, when BSA was substituted for CP, no competition for binding of C1q was detected (FIG. 1, shown as triangles), and the same lack of competition was seen with aldolase and egg albumin (data not shown). In addition, no binding was seen when BSA was coated on the plate in place of HNP-1. Although not bound by any theory, this data is consistent with HNP-1 and CP binding C1q in a comparable manner to regulate classical pathway activation (Hair et al., 2010. *J. Virol.* 82, 817-827).

Example 11—Identification of a CP Peptide with Homology to HNP-1 that Competes with WT CP for Binding to C1q Because CP efficiently competed with HNP-1 for binding to C1q, it was analyzed whether CP and HNP-1 shared any homology at the amino acid sequence level. Alignment of the 787 amino acid CP molecule with the 30 amino acid HNP-1 peptide was performed using Clustal W (Larkin et al., 2007. *Bioinformatics*. 23, 2947-2948). A region of homology was observed between HNP-1 and residues 79-139 of the CP molecule (FIG. 2A). To ascertain whether this CP sequence retained the complement regulation functions of WT CP, two 30 residue peptides were synthesized which encoded residues 79-108 (CP1) and 109-138 (CP2) of the CP molecule (FIG. 2A). CP1 aligned with the first 10 residues of HNP-1, whereas CP2 aligned with the last 20 residues. To ascertain whether peptides CP1 and CP2 could directly bind C1q and compete with WT CP for binding to C1q, a competition ELISA was performed in which CP1 and CP2 were coated on the ELISA plate. A fixed amount of purified C1q and increasing amounts of WT CP were added simultaneously, and bound C1q was then detected with polyclonal antibody to C1q. In the absence of CP, C1q was efficiently bound by CP1 peptide; however, the C1q signal decreased with increasing amounts of CP, indicating that CP dose-dependently competed with CP1 for C1q binding (FIG. 2B, shown as a stippled line). When BSA was substituted for CP under the same conditions, CP1 bound efficiently to C1q and no competition was observed (FIG. 2B, shown in triangles). In contrast to CP1, CP2 did not compete for C1q binding (FIG. 2B, shown in squares). Thus, CP residues 79-108 were sufficient to bind C1q in a similar manner to WT CP.

Example 12—Binding of CP Peptide Derivatives to C1q

The ability of the CP1 peptide to competitively bind C1q in a similar fashion to WT CP led to an initial analysis of the peptide residues that are critical for these activities. Targeted amino acid substitutions and a large deletion of the parent CP1 peptide were synthesized, as shown in TABLE 1 above. C04A and C27A were designed to assess whether putative disulphide bonding between the two cysteine residues in CP1 were required for C1q binding and regulating complement activation. E23A and E25A were synthesized to assess whether these negatively charged glutamic acid residues were required for C1q binding and complement regulation. Finally, a peptide deleting internal residues 8-22 (Δ8-22) was designed to determine if this region, which does not have homology with HNP-1, was required for C1q binding and regulating complement activation. This peptide, Δ8-22, retained the two cysteine and two glutamic acid residues.

To ascertain whether these peptides could bind C1q, binding assays in which the various peptide derivatives were coated on an ELISA plate were performed. Increasing amounts of purified C1q was added and bound C1q was then detected with polyclonal antibody to C1q. CP1 dose-dependently bound C1q (FIG. 3A), consistent with its ability to compete with WT CP for C1q binding (FIG. 2B). CP2 bound C1q at similar levels to that of HNP-1 (FIG. 3A), demonstrating that while this peptide does not compete with CP for C1q binding, it does retain the ability to bind C1q, possibly as a result of its homology to the C-terminal 20 amino acids of HNP-1. The capacity of C04A and C27A to bind C1q was analyzed next, and both peptides bound C1q similarly to CP1 (FIG. 3B). E23A and E25A were found to bind C1q at levels between that of CP1 and CP2 (FIG. 3C), and this trend was also observed for peptide Δ8-22 (FIG. 3D).

In summary, while all of the CP1 derivative peptides bound C1q, the degree of binding varied depending on the amino acid substitution. While not bound by any theory, neither the cysteine (C04 and C27) nor the glutamic acid (E23 and E25) residues appeared to play a critical role in C1q binding. In addition, peptide Δ8-22, which has a deletion of the internal 15 amino acid residues of CP1, still retained C1q binding activity. Thus, the CP1 derivatives individually demonstrate that binding to C1q is not dependent on either glutamic acid residue nor on either cysteine residue, suggesting that cyclicalization via a disulphide bond is not required.

Example 13—CP1 Peptide Regulates C1s Activation

Figure 4A:
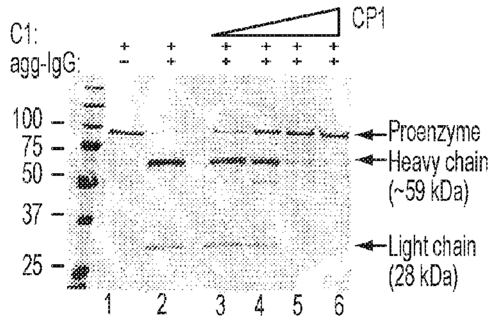
FIGS. 4A-4D demonstrate that CP1, but not CP2, regulates C1 activation. Partially purified human C1 was incubated alone, with aggregated IgG (agg-IgG), or with agg-IgG and increasing amounts of CP1 (FIG. 4A) or CP2 (FIG. 4B) peptides (1-4 μl of a 250 mM stock) for 90 minutes at 37° C. The reaction mixtures were then loaded on an 8% SDS-PAGE gel and subjected to immunoblot with polyclonal antisera to C1s.
Figure 4B:
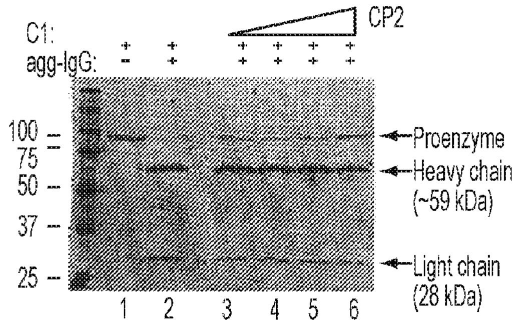
Figure 4C:
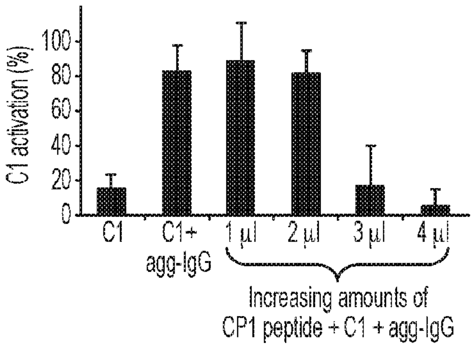
Figure 4D:
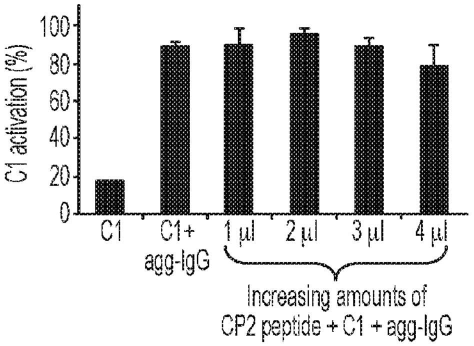

Purified CP can regulate classical pathway activation at the level of C1, by binding C1q and preventing the cleavage of the proenzyme C1s (Hair et al., 2010. *J. Virol.* 82, 817-827). To evaluate if CP1 and CP2 peptides were capable of regulating C1 activation as well, partially purified C1 complex was incubated for 90 minutes at 37° C. with heat-aggregated IgG (a potent stimulator of classical pathway activation) with increasing amounts of CP1 and CP2. To evaluate C1s activation, the cleavage of proenzyme C1s into the heavy and light chains was detected. C1 incubated alone showed minimal spontaneous activation of C1s, whereas C1 in the presence of heat-aggregated IgG demonstrated robust C1s cleavage (FIG. 4A, lanes 1 and 2). Incubating C1 and heat-aggregated IgG with increasing amounts of CP1 dose-dependently suppressed C1s cleavage (FIG. 4A, lanes 3-6) to levels observed for spontaneous C1 activation (FIG. 4A, lane 1). In contrast to CP1, CP2 did not demonstrate significant regulation of C1s cleavage at any of the concentrations tested (FIG. 4B, lanes 3-6). Quantification by Odyssey imaging of the regulation of C1s cleavage for CP1 and CP2 in two independent experiments for each peptide validated these results (FIGS. 4C-4D). While CP2 demonstrated minimal binding to C1q (FIG. 3A) and did not demonstrate the capacity to regulate C1s cleavage (FIGS. 4B and 4D), it was tested whether a combination of CP1 and CP2 would result in greater regulation of C1s cleavage than CP1 alone. CP1 and CP2 together resulted in no more regulation of C1s cleavage than that observed for CP1 alone. Consistent with the ability of the peptide derivatives to bind C1q, all peptide derivatives of CP1 were also found to inhibit C1s activation as demonstrated for CP1 (data not shown). While not bound by any theory, the ability of CP1 to regulate activation at the first component of the classical pathway, C1, suggests that this peptide regulates classical pathway activation in a comparable fashion to WT CP.

Example 14—Regulation of Complement Activity by CP Peptide in Functional Assays

To determine the ability of the peptide compounds to regulate complement activation in functional assays, a C4 activation assay and a hemolytic assay were used. For the C4 activation assay, a method known in the art (Mallik et al., 2005. *J. Med. Chem.* 48, 274-286) was modified so that ELISA plates were coated with ovalbumin to which anti-ovalbumin antibodies were allowed to bind, mimicking an immune-complex target. The various peptide compounds were then diluted to 0.5 mM in 10% NHS/GVBS$^{++}$, incubated for 15 minutes, and subsequently added to each well. Classical pathway activation (C4) was assayed by detecting deposition of C4-fragments using a polyclonal anti-C4 antibody. As shown in FIG. 5, NHS alone, NHS+BSA, and NHS+DMSO all demonstrated similar deposition of C4-fragments, whereas NHS treated with WT CP regulated C4 activation. CP1 demonstrated a 35% inhibitory effect, whereas CP2 had no effect on C4 activation, consistent with the results observed for C1s activation (FIG. 4). Peptide compounds C04A, C27A, E25A, and Δ8-22 all inhibited complement activation of C4 by 20-45%. E23A potently suppressed C4 activation by 90%.

Peptide compound regulation of serum complement activity was assessed in a standard hemolytic complement assay. Sheep erythrocytes were sensitized with antibody and incubated with NHS, with or without peptide pre-incubation, and hemolytic complement activity was measured. As opposed to the C4 activation assay, all three complement pathways (classical, lectin and alternative) were present and may have contributed to the observed regulatory activity. However, initial complement activation was primarily driven by the antibody on the erythrocytes and, thus, the classical pathway. As demonstrated in FIG. 6A, NHS either alone or in the presence of DMSO lysed erythrocytes as expected. CP2 regulated lysis to a similar level as CP1 (66% inhibition) in contrast to the C4 activation assay, in which the CP2 peptide had no regulatory effect. C04A had minimal effect on erythrocyte lysis, whereas C27A was more inhibitory (85% inhibition). Similar to the effect seen in the C4 activation assay, E23A inhibited erythrocyte lysis efficiently (85% inhibition) compared with E25A, which had 60% inhibition. The Δ8-22 peptide compound inhibited erythrocyte lysis by 75%.

To test whether the peptides were regulating alternative pathway activation, the amount of serum used during the pre-incubation was increased, effectively lowering the concentration of the peptides tested to 0.77 mM, such that minimal inhibition occurred in NHS (FIG. 6B). The regulatory activity of the peptides on the classical pathway alone was then assessed by using factor B-depleted serum in the hemolytic assay, utilizing the same amounts of peptide and serum (FIG. 6B). In contrast to the lack of regulation seen for NHS, the parental peptide CP1 regulated classical complement pathway activation in factor B-depleted serum. In addition, peptide compounds E23A, E25A, and Δ8-22 regulated classical complement pathway activation significantly. While not bound by any theory, at higher amounts of serum, where the alternative pathway begins to be more efficiently activated, several peptides continued to efficiently regulate classical pathway activation, but not overall complement activation, suggesting the alternative pathway is mediating hemolysis. Comparison of the regulatory activity from FIGS. 5 and 6 indicate that E23A effects good regulation of complement.

The Polar Assortant peptide initially showed significant regulation of classical pathway activity in a hemolytic assay with NHS and factor B-depleted serum (data not shown). To further explore the regulatory activity of this peptide on the classical pathway, a dilution of the Polar Assortant peptide was made in factor B-depleted serum. In contrast to the lack of regulation seen for NHS alone and DMSO vehicle, the Polar Assortant peptide dose-dependently regulated classical pathway activation significantly beyond that of Δ8-22 (FIG. 7, compare 0.77 mM Δ8-22 versus 0.77 mM Polar Assortant).

Example 15—CP Peptides do not Oligomerize into Higher Order Structures

Figure 8A:
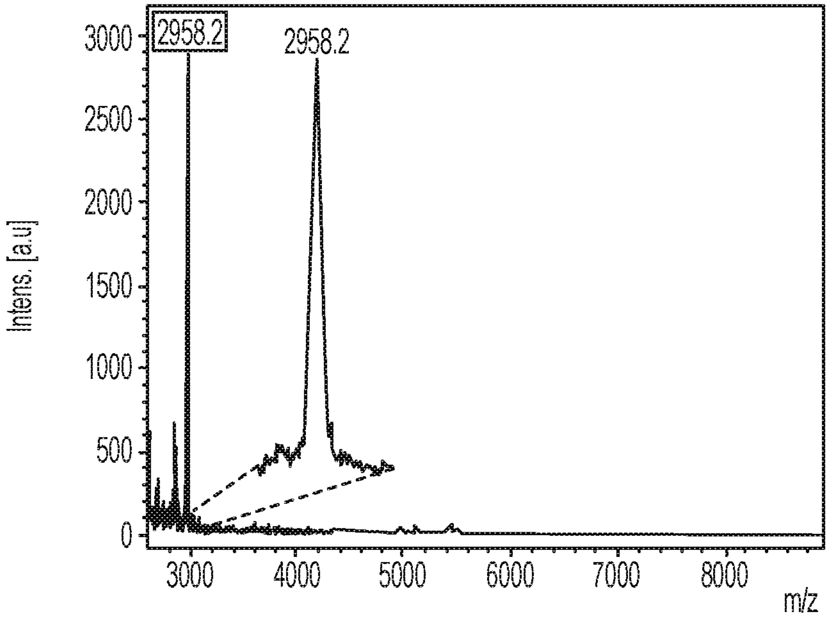
FIGS. 8A and B are graphs depicting MALDI-TOF-TOF mass spectrometry analysis of the oligomeric state of E23A.
Figure 8B:
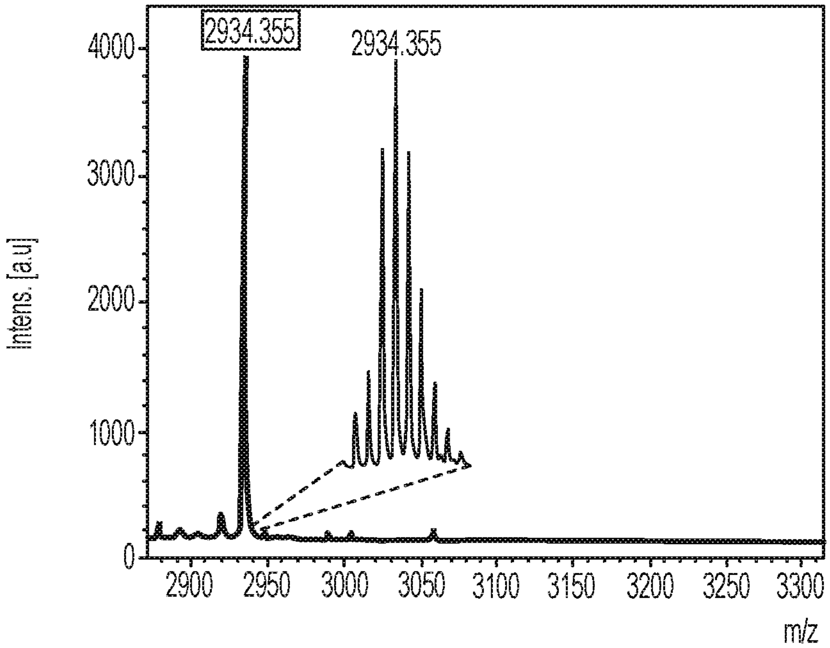
FIG. 8B depicts reflection mode analysis of E23A. E23A has a theoretical mass of 2934.37.

To further characterize the CP peptides, it was assessed whether these compounds could oligomerize into higher ordered structures, such as dimers, trimers, etc. To assess CP peptide oligomerization, all seven CP peptides from TABLE 1 were analyzed by MALDI-TOF-TOF mass spectrometry in the linear and reflection modes. In both modes, all peptides were found to be monomeric with no major peaks carrying a mass to charge ratio (m/z) greater than the theoretical mass of the peptide tested. FIGS. 8A-8B show both the linear and reflection modes, respectively. While the linear mode is lower resolution than the reflection mode, both modes demonstrate that E23A is monomeric with no other higher-order peaks evident.

Example 16—Structural Model for E23A Based on Homology with the Plant Defensin VrD1

Given the identification of E23A as a highly potent regulator of classical pathway activation, a structural model for the E23A peptide was generated. The amino acid sequence of E23A was uploaded onto the CPHmodels-3.0 server. This program is a protein homology modeling resource where template recognition is based upon profile-profile alignment guided by secondary structure and exposure predictions (Lund et al., 2002. Abstract at the CASP5 conference A102). Consistent with the homology discussed above between CP and HNP-1, CPHmodels 3.0 aligned residues 2-29 of E23A to residues 17-44 of the 46 residue plant defensin, *Vigna radiata* plant defensin 1 (VrD1) (FIG. 9A). Based upon the nuclear magnetic resonance solution structure of VrD1 (Liu et al., 2006. *Proteins.* 63, 777-786), a model of the E23A was generated by CPHmodels 3.0 and displayed in FirstGlance in JMol (FIG. 9B). FIG. 9A depicts an 11 residue N-terminal alpha helix followed by two anti-parallel beta strands. The alpha helix and beta strands are connected by two, 3-5 residue disordered loops. The two cysteine residues are shown forming a disulphide bond (depicted as a thin cylinder) between the alpha helix and second beta strand, which may play a role in stabilizing the overall structure.

Rational Peptide Compound Design

Example 17—Synthesis of Peptide Analogs of CP1

The peptide analogs of CP1 are commercially synthesized. These modified peptides are then analyzed for interaction with C1q and MBL in binding assays known in the art (Hair et al., 2010. *Molec. Immunol.* 47, 792-798).). These assays are briefly described below.

Example 18—C1q Binding

CP peptide analogs are coated onto microtiter plates at various concentrations and analyzed for their ability to bind purified C1q (CompTech). C1q binding is detected with anti-C1q monoclonal antibody (Quidel), followed by donkey anti-mouse HRP (Santa Cruz Biotech). The plates are then developed with tetramethyl benzindine, the reactions terminated with $H_2SO_4$, and absorbance read at 450 nm. A positive control for C1q binding consists of CP1, whereas negative controls are BSA. The initial conditions for the binding of each peptide are determined, and then serial dilutions of the peptides are performed in triplicate to determine statistical significance and calculate half-maximal binding values as previously reported (Hair et al., 2010. *Molec. Immunol.* 47, 792-798). Half-maximal binding values are used to evaluate the relative binding affinity of each peptide analog.

Example 19—MBL Binding

MBL binding is conducted in a similar manner to the C1q binding assay described above. Purified human MBL and goat anti-MBL sera are utilized, followed by donkey anti-goat HRP for detection of MBL. Again, half-maximal binding values are calculated and compared across peptide compounds.

The ability of CP peptide derivatives to inhibit C1 and MBL activation in functional assays is tested. The CP peptide analogs that specifically bind to C1q and MBL are assessed for their capacity to inhibit classical and lectin pathway activation in functional assays. In addition to specific assays for inhibition of C1 and MBL, an antibody-initiated complement activation assay is utilized to determine IC50 values of the peptide analogs in both human and rat serum. This allows for direct comparison of the relative functional activity of the peptides.

Example 20—C1 Activation Assay

The peptide compounds are analyzed for their ability to inhibit C1 activation in the C1s immunoblot cleavage assay. C1 (CompTech) and heat-aggregated IgG are incubated with increasing amounts of the peptides. C1s is detected with a goat polyclonal antibody to C1s (Quidel), followed by an infrared dye conjugated donkey anti-goat antibody (Li-Cor Biosciences) for analysis on an Odyssey infrared imaging system (Li-Cor Biosciences). C1 in the absence or presence of heat-aggregated IgG is included on each blot as a negative and positive control for C1s cleavage, respectively. To compare the extent of inhibition of C1s cleavage by the various CP peptides, the C1s heavy and light chains are quantified relative to C1s precursor using the Odyssey 3.0 software and the percent of C1 activation is determined. CP1+heat-aggregated IgG serves as a positive control of inhibition of C1s cleavage and can also be used to normalize values between experiments, if necessary.

Example 21—MBL Activation Assay

A commercial MBL activation assay (HyCult) is used (Hair et al., 2010. *Molec. Immunol.* 47, 792-798) to evaluate the CP peptide analogs. Normal human serum (NHS) is incubated with increasing amounts of the peptides and evaluated for lectin pathway inhibition using the commercial kit. NHS alone serves as a positive control for lectin activation, whereas heat-inactivated NHS serves as a negative control for activation. NHS+CP are used as control for demonstrating inhibition of lectin pathway activation.

Alternatively, a lectin activation assay known in the art (Groeneveld et al., 2007. *Molec. Immunol.* 44, 3608-3614) is used to evaluate the peptide compounds.

Example 22—Antibody-Initiated Serum Complement Activation Assay

To directly compare the inhibitory activity of CP1 and its peptide analogs, an antibody-initiated serum complement activation assay is used. This assay is a modification of protocol utilized by Dr. John Lambris and colleagues (University of Pennsylvania) to calculate $IC_{50}$ values of Compstatin and its analogs (Mallik et al., 2005. *J. Med. Chem.* 48, 274-286). Complement activation inhibition is assessed by measuring the inhibition of serum C4 fixation to ovalbumin-anti-ovalbumin complexes in NHS. Microtiter wells are coated with ovalbumin (10 mg/ml). Wells are then saturated with BSA (10 mg/ml) for one hour at room temperature and a 1:2,000 dilution of rabbit anti-ovalbumin antibody added to form immunocomplexes by which complement can be activated. Peptides at various concentrations are then added directly to each well, followed by a 1:80 dilution of NHS in GVB++. After a 30 minute incubation, bound C4 is detected using a 1:2,000 dilution of a goat anti-C4 antibody, followed by a 1:2,500 dilution of donkey anti-goat HRP secondary antibody. The plates are then developed with tetramethyl benzindine, the reactions terminated with $H_2SO_4$, and absorbance read at 450 nm. Percent inhibition is normalized by considering 100% activation equal to activation occurring in the absence of peptide. Heat-inactivated NHS is utilized as a negative control for activation. NHS+CP1 are used as a control of inhibition of activation.

$IC_{50}$ values for the selected peptide compounds are determined by plotting the percent inhibition against peptide concentration. CP inhibits C4 activation via the classical and lectin pathways, and CP has nominal effects on activation of the alternative pathway (Bonaparte et al., 2008. *J. Virol.* 82, 817-827, Hair et al., 2010. *Molec. Immunol.* 47, 792-798). Using CP1 as the benchmark, the relative inhibitory activities for all peptide compounds are thus directly determined.

The $IC_{50}$ values for the CP peptides in normal rat sera (NRS) are determined. Wild-type CP and CP1 have been demonstrated to suppress antibody-initiated complement activation in NRS (Hair et al., 2010. *Molec. Immunol.* 47, 792-798). Determination of the $IC_{50}$ values for the peptide compounds in NRS are critical for dose-ranging experiments in rats.

Other aspects, modifications, and embodiments are within the scope of the following claims.

REFERENCES

1. Bonaparte, R. S., Hair, P. S., Banthia, D., Marshall, D. M., Cunnion, K. M., Krishna, N. K. 2008. Human astrovirus coat protein inhibits serum complement activation via C1, the first component of the classical pathway. J. Virol. 82, 817-827.
2. Carvalho A. O., Gomes, V. M. 2009. Plant defensins—prospects for the biological functions and biotechnological properties. Peptides. 30, 1007-1020.
3. Castellano, G., Melchiorre, R., Loverre, A., Ditonno, P., Montinaro, V., Rossini, M., Divella, C., Battaglia, M., Lucarelli, G., Annunziata, G., Palazzo, S., Selvaggi, F. P., Staffieri, F., Crovace, A., Daha, M. R., Mannesse, M., van Wetering, S., Schena, F. P., Grandaliano, G. 2010. Therapeutic targeting of classical and lectin pathways of complement protects from ischemia-reperfusion-induced renal damage. Amer. J. Pathol. 176, 1-12.

4. Cunnion, K M., Lee, J. C., Frank, M. M. 2001. Capsule production and growth phase influence binding of complement to *Staphylococcus aureus*. Infect. Immun. 69, 6796-6803.
5. Fryer J. P., Leventhal, J. R., Pao, W., Stadler, C., Jones, M., Walsh, T., Zhong, R., Zhang, Z., Wang, H., Goodman, D. J., Kurek, M., d'Apice, A. J., Blondin, B., Ivancic, D., Buckingham, F., Kaufman, D., Abecassis, M., Stuart, F., Anderson, B. E. 2000. Synthetic peptides which inhibit the interaction between C1q and immunoglobulin and prolong xenograft survival. Transplanatation. 70, 828-836.
6. Groeneveld, T. W. L., Ramwadhdoebé, T. H., Trouw, L. A., van den Ham, D. L., van der Borden, V., Drijfhout, J. W., Hiemstra, P. S., Daha, M. R., Roos, A. 2007. Human neutrophil peptide-1 inhibits both the classical and the lectin pathway of complement activation. Molec. Immunol. 44, 3608-3614.
7. Hair, P. S., Gronemus, J. Q., Crawford, K. B., Salvi, V. P., Cunnion, K. M., Thielens, N. M., Arlaud, G. J., Rawal, N., Krishna, N. K. 2010. Human astrovirus coat protein binds C1q and MBL and inhibits the classical and lectin pathways of complement activation. Molec. Immunol. 47, 792-798.
8. Huwiler, K. G., Mosher, D. F., Vestling, M. M. 2003. Optimizing the MALDI-TOF-MS observation of peptides containing disulphide bonds. J. Biomolec. Tech. 14, 289-297.
9. Kojima, T., Del Carpio C. A., Tajiri, H., Yoshikawa, K., Saga, S., Yokoyama, I. 1999.

Inhibition of complement-mediated immune hemolysis by peptides derived from the constant domain of immunoglobulin. Transplantation. 67, 637-638.

10. Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. Clustal W and Clustal X version 2.0. Bioinformatics. 23, 2947-2948.
11. Lauvrak, V., Brekke, O. H., Ihle, Ø., Lindqvist, B. H. 1997. Identification and characterization of C1q-binding phage displayed peptides. Biol. Chem. 378, 1509-1519.
12. Lee, H., Green, D. J., Lai, L., Hou, Y. J., Jensenius, J. C., Liu, D., Cheong, C., Park, C. G., Zhang, M. 2010. Early complement factors in the local tissue immunocomplex generated during intestinal ischemia/reperfusion injury. Mol. Immunol. 47, 972-981.
13. Liu, Y. J., Cheng, C. S., Lai, S. M., Hsu, M. P., Chen, C. S., Lyu, P. C. 2006. Solution structure of the plant defensin VrD1 from mung bean and its possible role in insecticidal activity against bruchids. Proteins. 63, 777-786.
14. Lund, O., Nielsen, M., Lundegaard, C., Worning, P. 2002. CPHmodels 2.0: X3M a Computer Program to Extract 3D Models. Abstract at the CASP5 conference A102.
15. Mallik, B., Katragadda, M., Spruce, L. A., Carafides, C., Tsokos, C. G., Morikis D., Lambris, J. D. 2005. Design and NMR characterization of active analogs of Compstatin containing non-natural amino acids. J. Med. Chem. 48, 274-286.
16. Messmer, B. T., Benham, C. J., Thaler, D. S. 2000. Sequential determination of ligands binding to discrete components in heterogeneous mixtures by iterative panning and blocking (IPAB). J. Mol. Biol. 296, 821-832.
17. Ricklin, D., Lambris, J. D. 2007. Complement-targeted therapeutics. Nat. Biotech. 25, 1265-1275.
18. Roos, A., Nauta, A. J., Broers, D., Faber-Krol, M. C., Trouw, L. A., Drijfhout, J. W., Daha, M. R. 2001. Specific inhibition of the classical complement pathway by C1q-binding peptides. J. Immunol. 167, 7052-7059.
19. Sahu, A., Kay, B. K., Lambris, J. D. 1996. Inhibition of complement by a C3-binding peptide isolated from a phage-displayed random peptide library. J. Immunol. 157, 884-891.
20. Taylor K., Barran, P. E., Dorin, J. R. 2007. Structure—activity relationships in beta-defensin peptides. Biopolymers. 90, 1-7.
21. Tjernberg, J., Ekdahl, K. N., Lambris, J. D., Korsgren, O., Nilsson, B. 2008. Acute antibody-mediated complement activation mediates lysis of pancreatic islets cells and may cause tissue loss in clinical islet transplantation. Transplantation. 85, 1193-1199.
22. van den Berg, R. H., Faber-Krol, M. C., van Wetering, S. P., Hiemstra, S., Daha, M. R. 1998. Inhibition of activation of the classical pathway of complement by human neutrophil defensins. Blood. 92, 3898-3903.
23. Zhang, M., Takahashi, K., Alicot, E. M., Vorup-Jensen, T., Kessler, B., Thiel, S., Jensenius, J. C., Ezekowitz, R. A., Moore, F. D., Carroll, M. C. 2006. Activation of the lectin pathway by natural IgM in a model of ischemia/reperfusion injury. J. Immunol. 177, 4727-4734.
24. Zhang, X.-L., Selsted, M. E., Pardi, A. 1992. NMR studies of defensin antimicrobial peptides. 1. Resonance assignment and secondary structure determination of rabbit NP-2 and human HNP-1. Biochemistry. 31, 11348-11356.

The invention claimed is:

1. A peptide comprising the amino acid sequence of SEQ ID NO: 9, optionally with one or two conservative amino acid substitutions.

2. The peptide of claim 1, comprising an N-terminal acetylation.

3. A pharmaceutical composition comprising a therapeutically effective amount of the peptide of claim 1 and at least one pharmaceutically acceptable carrier, diluent, or excipient.

4. A pharmaceutical composition comprising a therapeutically effective amount of the peptide of claim 2 and at least one pharmaceutically acceptable carrier, diluent, or excipient.

* * * * *

SEQUENCE LISTING

```
<160> NUMBER OF SEQ ID NOS: 38

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Pro Ala Ile Cys Gln Arg Ala Thr Ala Thr Leu Gly Thr Val Gly Ser
1               5                   10                  15

Asn Thr Ser Gly Thr Thr Glu Ile Glu Ala Cys Ile Leu Leu
```

-continued

```
            20                  25                  30


<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asn Pro Val Leu Val Lys Asp Ala Thr Gly Ser Thr Gln Phe Gly Pro
1               5                   10                  15

Val Gln Ala Leu Gly Ala Gln Tyr Ser Met Trp Lys Leu Lys
            20                  25                  30


<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Pro Ala Ile Ala Gln Arg Ala Thr Ala Thr Leu Gly Thr Val Gly Ser
1               5                   10                  15

Asn Thr Ser Gly Thr Thr Glu Ile Glu Ala Cys Ile Leu Leu
            20                  25                  30


<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Pro Ala Ile Cys Gln Arg Ala Thr Ala Thr Leu Gly Thr Val Gly Ser
1               5                   10                  15

Asn Thr Ser Gly Thr Thr Glu Ile Glu Ala Ala Ile Leu Leu
            20                  25                  30


<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Pro Ala Ile Cys Gln Arg Ala Thr Ala Thr Leu Gly Thr Val Gly Ser
1               5                   10                  15

Asn Thr Ser Gly Thr Thr Ala Ile Glu Ala Cys Ile Leu Leu
            20                  25                  30


<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 6

Pro Ala Ile Cys Gln Arg Ala Thr Ala Thr Leu Gly Thr Val Gly Ser
1 5 10 15

Asn Thr Ser Gly Thr Thr Glu Ile Ala Ala Cys Ile Leu Leu
20 25 30

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Pro Ala Ile Cys Gln Arg Ala Glu Ile Glu Ala Cys Ile Leu Leu
1 5 10 15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Abu
<220> FEATURE:
<221> NAME/KEY: MOD_RES
<222> LOCATION: (12)..(12)
<223> OTHER INFORMATION: Abu

<400> SEQUENCE: 8

Pro Ala Ile Xaa Gln Arg Ala Glu Ile Glu Ala Xaa Ile Leu Leu
1 5 10 15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Ile Ala Leu Ile Leu Glu Pro Ile Cys Cys Gln Glu Arg Ala Ala
1 5 10 15

<210> SEQ ID NO 10
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Pro Ala Ile Cys Gln Arg Ala Thr Ala Thr Leu Gly Thr Asn Thr Ser
1 5 10 15

Gly Thr Thr Glu Ile Glu Ala Cys Ile Leu Leu
20 25

<210> SEQ ID NO 11
<211> LENGTH: 23
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 11

Pro Ala Ile Cys Gln Arg Ala Thr Ala Thr Leu Ser Gly Thr Thr Glu
1               5                   10                  15

Ile Glu Ala Cys Ile Leu Leu
            20


<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Ala Ile Cys Gln Arg Ala Thr Ala Thr Thr Glu Ile Glu Ala Cys
1               5                   10                  15

Ile Leu Leu


<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ile Cys Gln Arg Ala Thr Ala Thr Leu Gly Thr Val Gly Ser Asn
1               5                   10                  15

Thr Ser Gly Thr Thr Glu Ile Glu Ala Cys Ile Leu Leu
            20                  25


<210> SEQ ID NO 14
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Cys Gln Arg Ala Thr Ala Thr Leu Gly Thr Val Gly Ser Asn Thr
1               5                   10                  15

Ser Gly Thr Thr Glu Ile Glu Ala Cys Ile Leu Leu
            20                  25


<210> SEQ ID NO 15
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Gln Arg Ala Thr Ala Thr Leu Gly Thr Val Gly Ser Asn Thr Ser
1               5                   10                  15

Gly Thr Thr Glu Ile Glu Ala Cys Ile Leu Leu
            20                  25
```

-continued

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

```
Pro Ala Ile Cys Gln Arg Ala Thr Ala Thr Leu Gly Thr Val Gly Ser
1               5                   10                  15

Asn Thr Ser Gly Thr Thr Glu Ile Glu Ala Cys Ile Leu
            20                  25
```

<210> SEQ ID NO 17
<211> LENGTH: 28
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

```
Pro Ala Ile Cys Gln Arg Ala Thr Ala Thr Leu Gly Thr Val Gly Ser
1               5                   10                  15

Asn Thr Ser Gly Thr Thr Glu Ile Glu Ala Cys Ile
            20                  25
```

<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

```
Pro Ala Ile Cys Gln Arg Ala Thr Ala Thr Leu Gly Thr Val Gly Ser
1               5                   10                  15

Asn Thr Ser Gly Thr Thr Glu Ile Glu Ala Cys
            20                  25
```

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

```
Thr Ala Thr Leu Gly Thr Val Gly Ser Asn Thr Ser Gly Thr Thr
1               5                   10                  15
```

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

```
Thr Gly Ser Thr Gln Phe Gly Pro Val Gln Ala Leu Gly Ala Gln
1               5                   10                  15
```

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 21

```
Pro Ala Ile Ala Gln Arg Ala Thr Ala Thr Leu Gly Thr Val Gly Ser
1               5                   10                  15

Asn Thr Ser Gly Thr Thr Glu Ile Glu Ala Ala Ile Leu Leu
            20                  25                  30
```

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 22

```
Pro Ala Ile Cys Gln Arg Ala Thr Ala Thr Leu Gly Thr Val Gly Ser
1               5                   10                  15

Asn Thr Ser Gly Thr Thr Ala Ile Ala Ala Cys Ile Leu Leu
            20                  25                  30
```

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

```
Ala Ala Ile Cys Gln Arg Ala Glu Ile Glu Ala Cys Ile Leu Leu
1               5                   10                  15
```

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

```
Pro Ala Ala Cys Gln Arg Ala Glu Ile Glu Ala Cys Ile Leu Leu
1               5                   10                  15
```

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

```
Pro Ala Ile Ala Gln Arg Ala Glu Ile Glu Ala Cys Ile Leu Leu
1               5                   10                  15
```

<210> SEQ ID NO 26

-continued

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Ala Ile Cys Ala Arg Ala Glu Ile Glu Ala Cys Ile Leu Leu
1               5                   10                  15


<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Pro Ala Ile Cys Gln Ala Ala Glu Ile Glu Ala Cys Ile Leu Leu
1               5                   10                  15


<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Pro Ala Ile Cys Gln Arg Ala Ala Ile Glu Ala Cys Ile Leu Leu
1               5                   10                  15


<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Pro Ala Ile Cys Gln Arg Ala Glu Ala Glu Ala Cys Ile Leu Leu
1               5                   10                  15


<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Ala Ile Cys Gln Arg Ala Glu Ile Ala Ala Cys Ile Leu Leu
1               5                   10                  15


<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31
```

```
Pro Ala Ile Cys Gln Arg Ala Glu Ile Glu Ala Ala Ile Leu Leu
1               5                   10                  15


<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Ala Ile Cys Gln Arg Ala Glu Ile Glu Ala Cys Ala Leu Leu
1               5                   10                  15


<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Ala Ile Cys Gln Arg Ala Glu Ile Glu Ala Cys Ile Ala Leu
1               5                   10                  15


<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Pro Ala Ile Cys Gln Arg Ala Glu Ile Glu Ala Cys Ile Leu Ala
1               5                   10                  15


<210> SEQ ID NO 35
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-terminal acetylation

<400> SEQUENCE: 35

Pro Ala Ile Cys Gln Arg Ala Thr Ala Thr Leu Gly Thr Val Gly Ser
1               5                   10                  15

Asn Thr Ser Gly Thr Thr Glu Ile Glu Ala Cys Ile Leu Leu
            20                  25                  30


<210> SEQ ID NO 36
<211> LENGTH: 61
<212> TYPE: PRT
<213> ORGANISM: Human astrovirus

<400> SEQUENCE: 36

Pro Ala Ile Cys Gln Arg Ala Thr Ala Thr Leu Gly Thr Val Gly Ser
1               5                   10                  15

Asn Thr Ser Gly Thr Thr Glu Ile Glu Ala Cys Ile Leu Leu Asn Pro
            20                  25                  30

Val Leu Val Lys Asp Ala Thr Gly Ser Thr Gln Phe Gly Pro Val Gln
```

-continued

```
        35                  40                  45

Ala Leu Gly Ala Gln Tyr Ser Met Trp Lys Leu Lys Tyr
    50                  55                  60


<210> SEQ ID NO 37
<211> LENGTH: 30
<212> TYPE: PRT
<213> ORGANISM: Homo sapiens

<400> SEQUENCE: 37

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30


<210> SEQ ID NO 38
<211> LENGTH: 28
<212> TYPE: PRT
<213> ORGANISM: Vigna radiata

<400> SEQUENCE: 38

Thr Thr Cys Ala His Ser Cys Lys Asn Arg Gly Tyr Ile Gly Gly Asn
1               5                   10                  15

Cys Lys Gly Met Thr Arg Thr Cys Tyr Cys Leu Val
            20                  25
```